(12) United States Patent
Yeung et al.

(10) Patent No.: US 8,540,684 B2
(45) Date of Patent: Sep. 24, 2013

(54) BACK PAIN RELIEF AND IMMUNO PROTECTION OF DONOR CELLS

(75) Inventors: Jeffrey E. Yeung, San Jose, CA (US); Teresa T. Yeung, San Jose, CA (US)

(73) Assignee: Aleeva Medical Inc., San Jose, CA (US)

( * ) Notice: Subject to any disclaimer, the term of this patent is extended or adjusted under 35 U.S.C. 154(b) by 0 days.

(21) Appl. No.: 12/930,632

(22) Filed: Jan. 11, 2011

(65) Prior Publication Data

US 2011/0105988 A1    May 5, 2011

Related U.S. Application Data

(62) Division of application No. 10/555,895, filed as application No. PCT/US2004/014368 on May 7, 2004, now Pat. No. 8,226,600.

(51) Int. Cl.
*A61M 5/00* (2006.01)
*A61M 5/31* (2006.01)
*A61M 5/178* (2006.01)

(52) U.S. Cl.
USPC .......................................... 604/239; 604/158

(58) Field of Classification Search
USPC ............... 604/161–164, 192–194, 239–240, 604/158–159, 164.01–164.09; 606/108, 606/222–233
See application file for complete search history.

(56) References Cited

U.S. PATENT DOCUMENTS

| | | | | |
|---|---|---|---|---|
| 5,800,484 | A * | 9/1998 | Gough et al. | 607/104 |
| 6,224,630 | B1 * | 5/2001 | Bao et al. | 623/17.16 |
| 6,508,839 | B1 * | 1/2003 | Lambrecht et al. | 623/17.16 |

* cited by examiner

*Primary Examiner* — Theodore J Stigell
*Assistant Examiner* — Rebecca E Eisenberg
(74) *Attorney, Agent, or Firm* — Carol Titas; GSS Law Group

(57) ABSTRACT

The intervertebral disc is avascular. With aging, endplates become occluded by calcified layers, and diffusion of nutrients and oxygen into the disc diminishes. The disc degenerates, and pain ensues. Conduits are delivered and deployed into the intervertebral disc to re-establish the exchange of nutrients and waste between the disc and bodily circulation to stop or reverse disc degeneration and relieve pain. The intervertebral disc installed with semi-permeable conduits may be used as an immuno-isolated capsule to encapsulate donor cells capable of biosynthesizing therapeutic molecules. The semi-permeable conduits establish the exchange of nutrients and therapeutic molecules between disc and bodily circulation to treat a disease without using immuno-suppressive drugs.

24 Claims, 34 Drawing Sheets

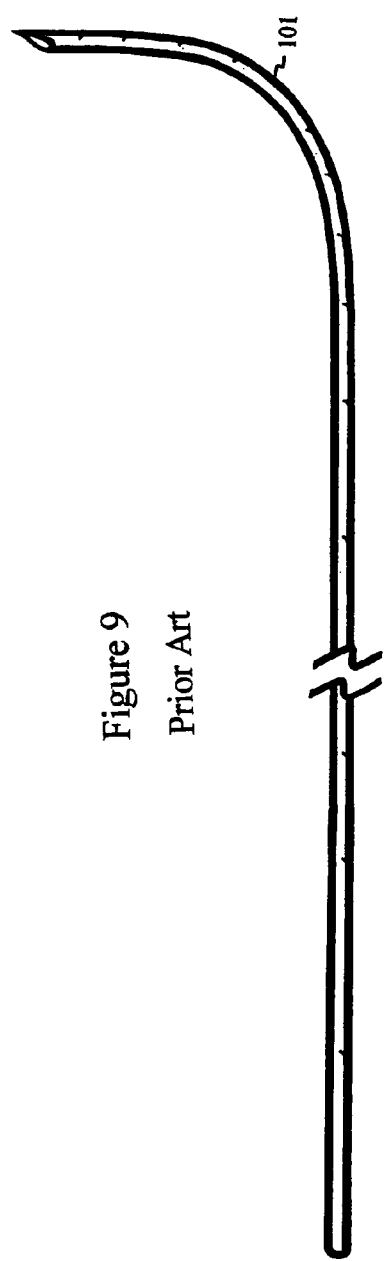
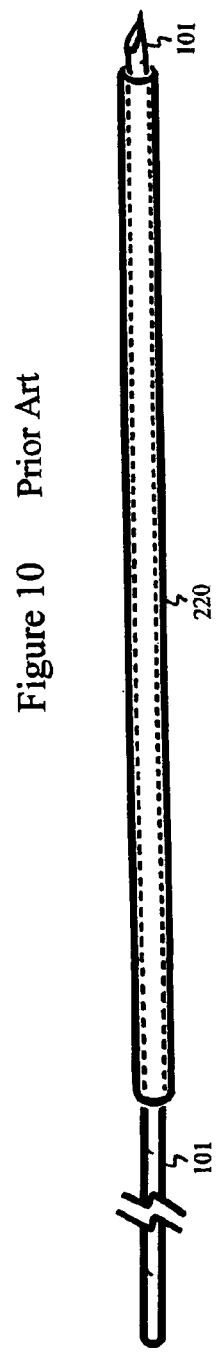
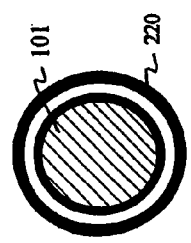
Figure 9 Prior Art
Figure 10 Prior Art
Figure 11 Prior Art

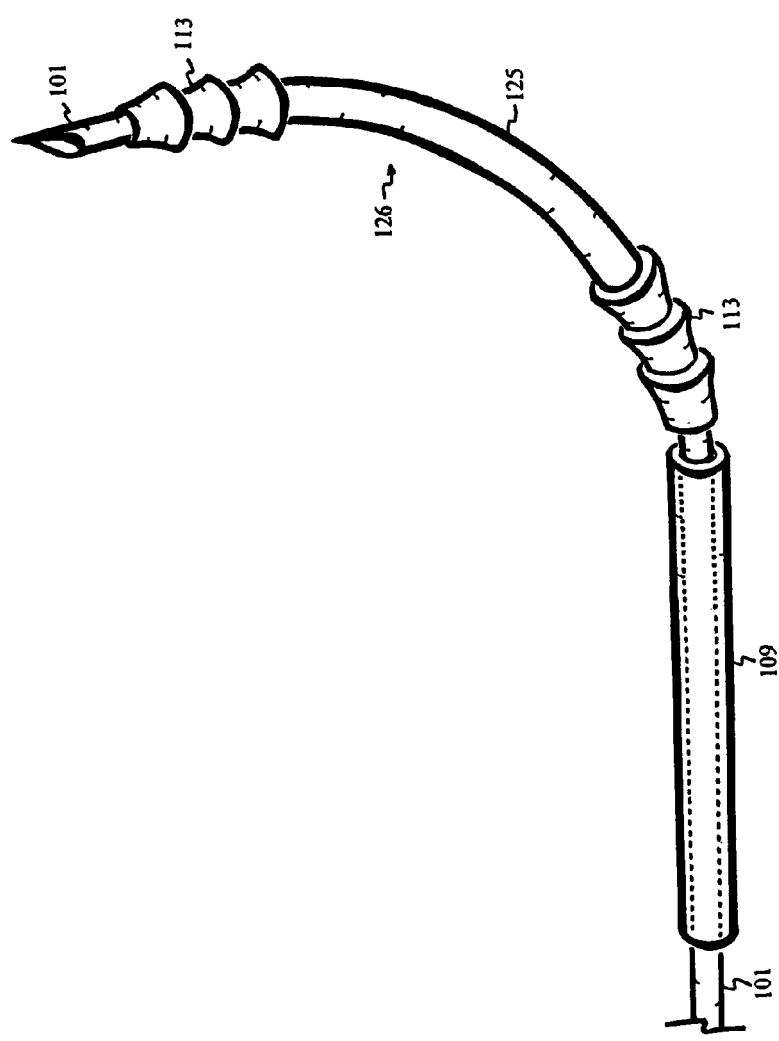
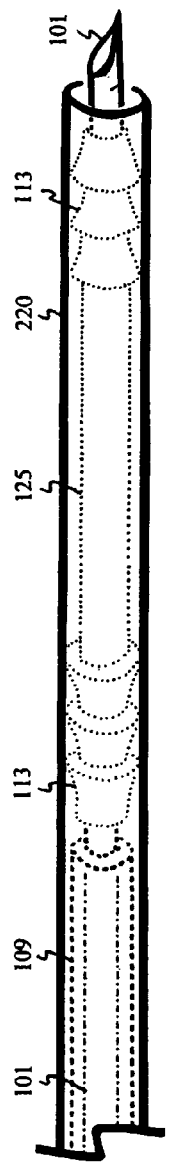
Figure 20
Figure 21

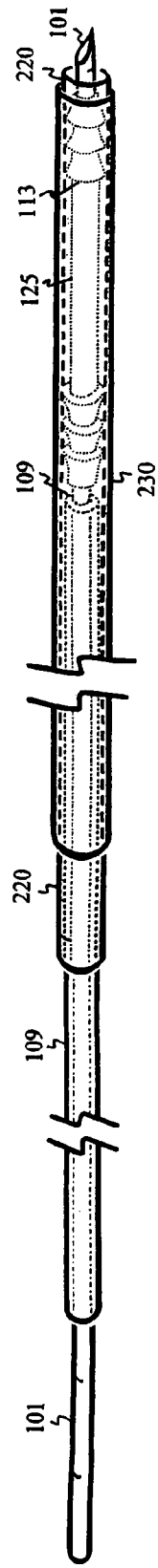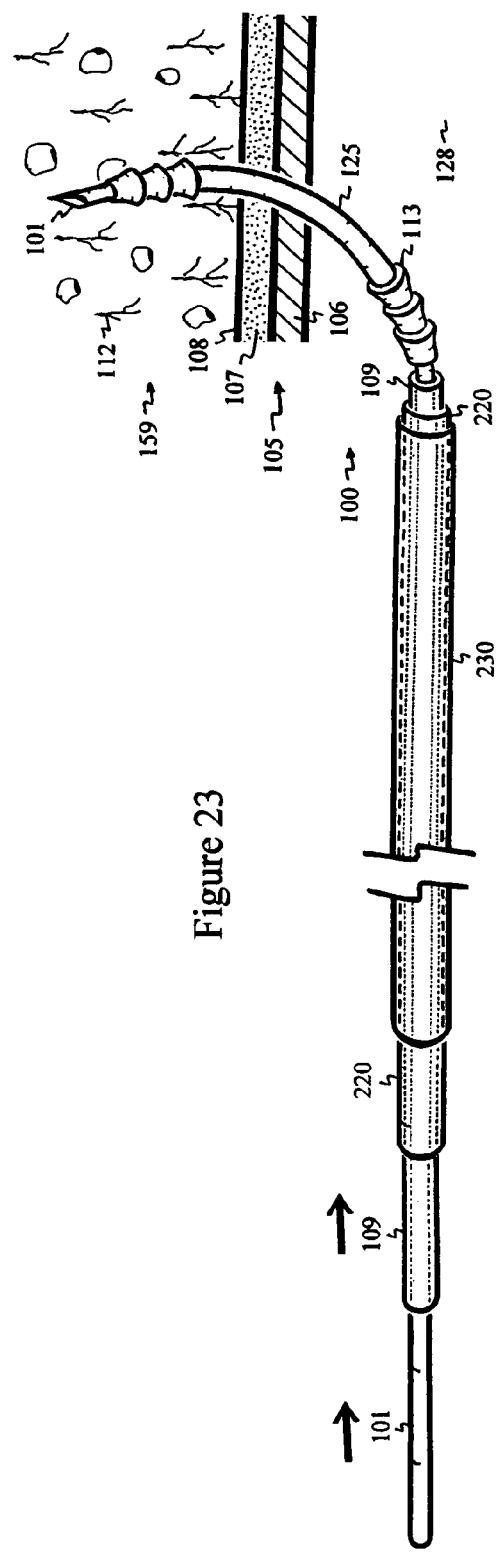

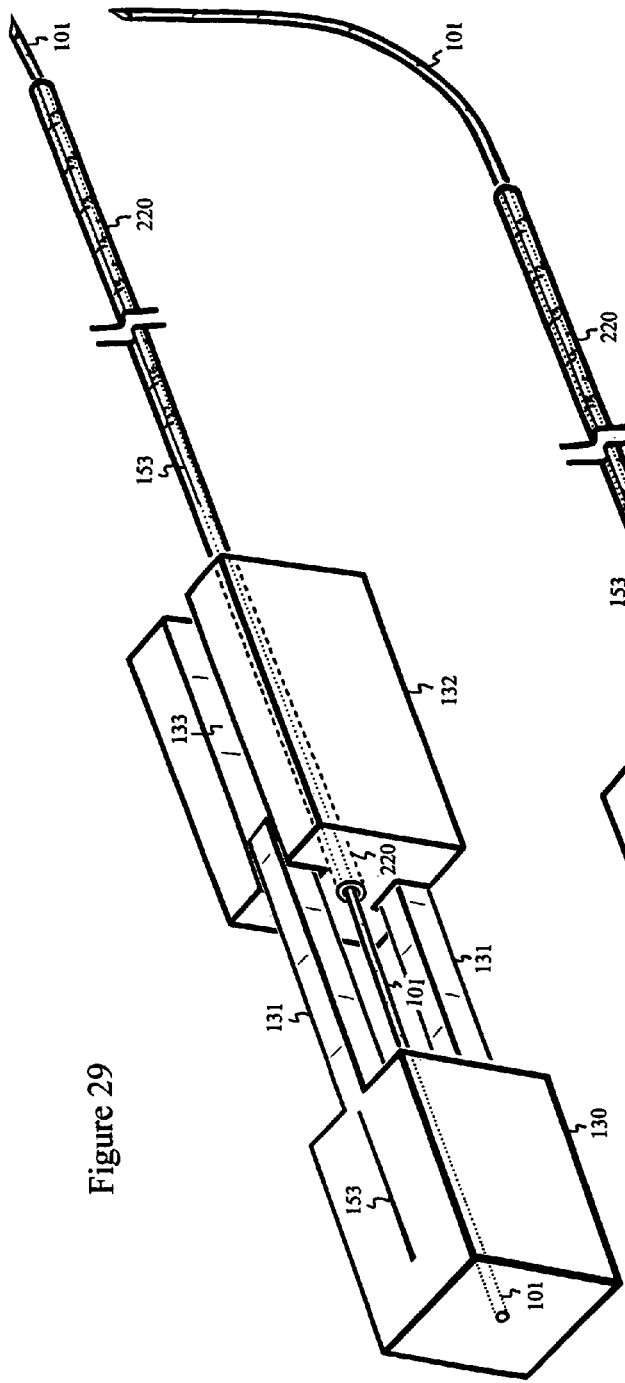

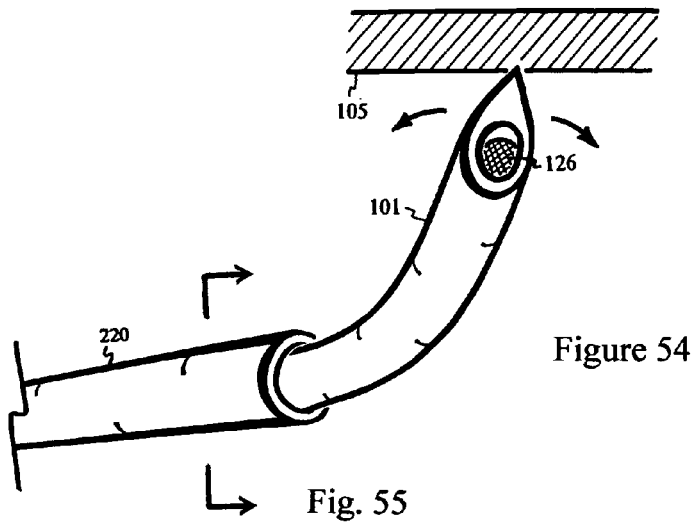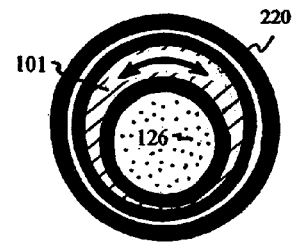
Figure 54
Figure 55
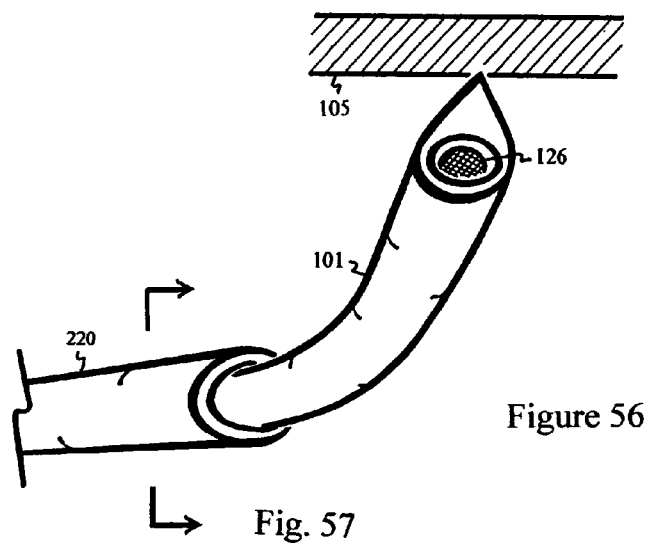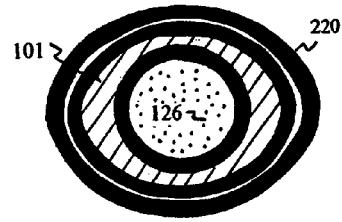
Figure 56
Figure 57
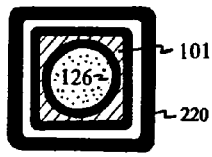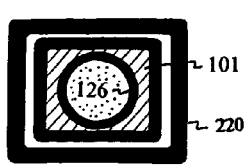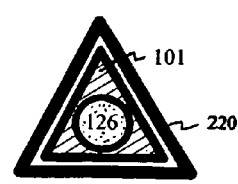
Figure 58
Figure 59
Figure 60

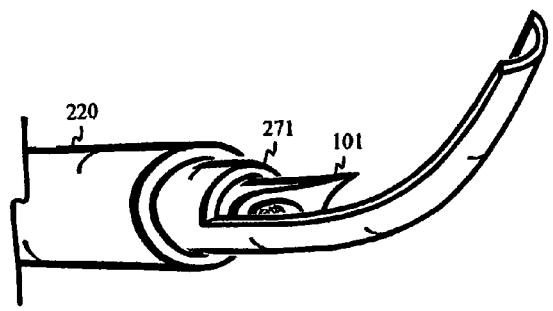
Figure 68
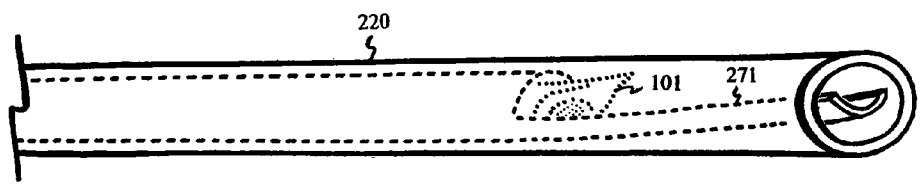
Figure 69
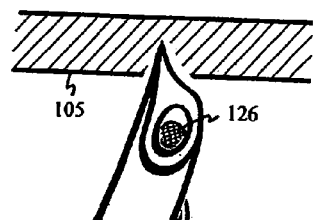
Figure 70
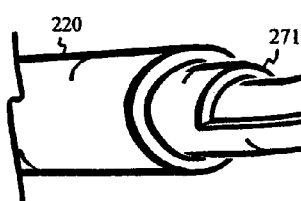
Figure 71

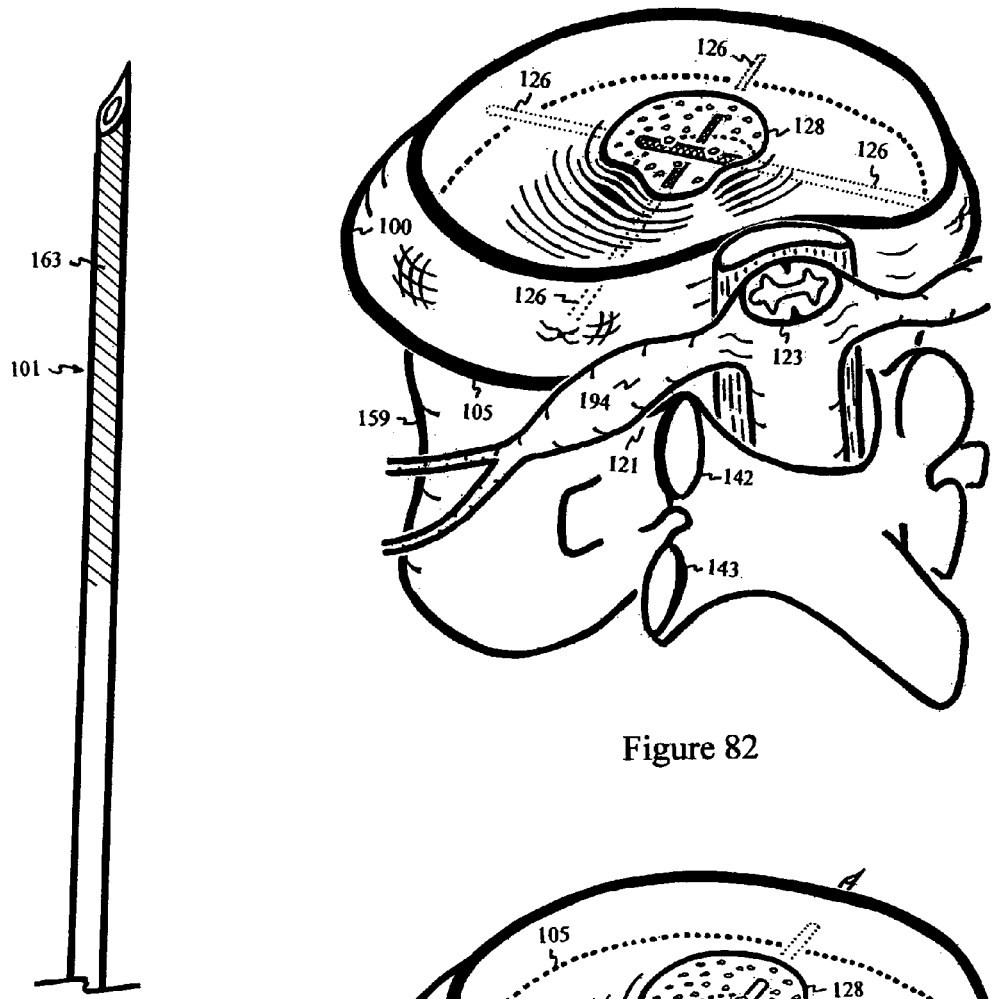
Figure 82
Figure 81
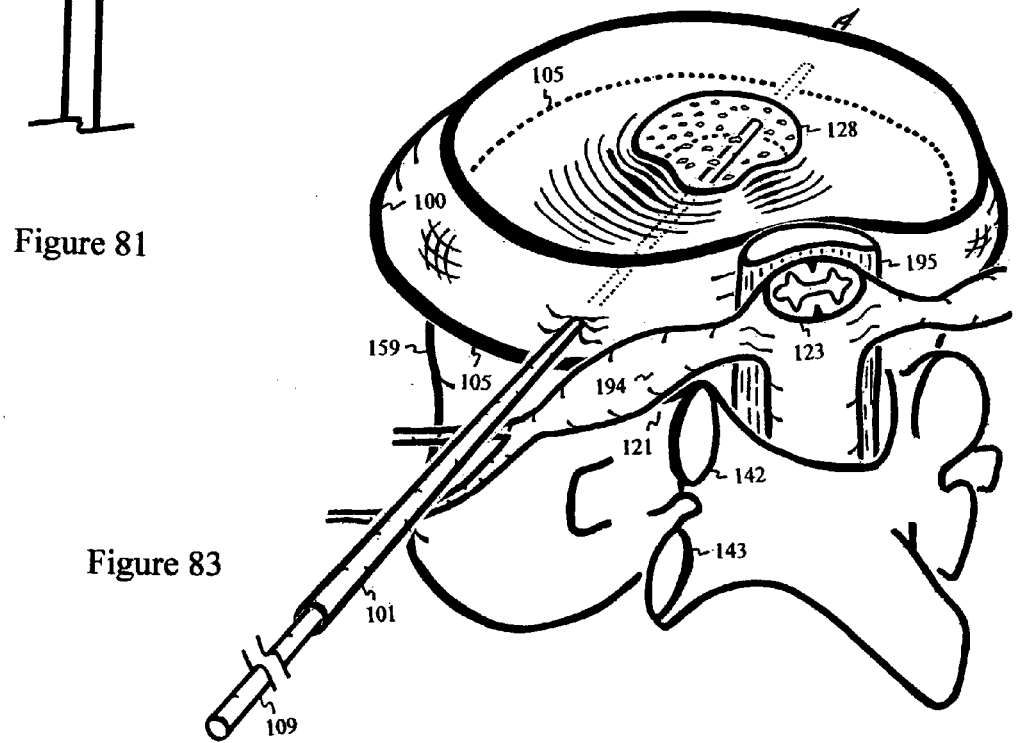
Figure 83

BACK PAIN RELIEF AND IMMUNO PROTECTION OF DONOR CELLS

CROSS-REFERENCES TO OTHER APPLICATIONS

This is a divisional application to U.S. Ser. No. 10/555,895 filed on Nov. 2, 2006, the national stage of PCT/US2004/14368 filed on May 7, 2004.

FIELD OF INVENTION

This invention relates to methods for transporting nutrients, waste and therapeutic molecules between the intervertebral disc and bodily circulation for back pain relief, disc regeneration and/or treating other diseases.

BACKGROUND

Low back pain is a leading cause of disability and lost productivity. Up to 90% of adults experience back pain at some time during their lives. For frequency of physician visits, back pain is second only to upper respiratory infections. In the United States the economic impact of this malady has been reported to range from $50-$100 billion each year, disabling 5.2 million people. Though the sources of low back pain are varied, in many cases the intervertebral disc is thought to play a central role. Degeneration of the disc initiates pain in other tissues by altering spinal mechanics and producing non-physiologic stress in surrounding tissues.

The intervertebral disc 100 absorbs most of the compressive load of the spine, but the facet joints 142, 143 of the vertebral bodies 159 share approximately 16%. The disc 100 consists of three distinct parts: the nucleus pulposus 128, the annular layers and the cartilaginous endplates 105, as shown in FIGS. 1 and 2. The disc 100 maintains its structural properties largely through its ability to attract and retain water. A normal disc 100 contains 80% water in the nucleus pulposus 128. The nucleus pulposus 128 within a normal disc 100 is rich in water absorbing sulfated glycosaminoglycans, creating the swelling pressure to provide tensile stress within the collagen fibers of the annulus. The swelling pressure produced by high water content is crucial to supporting the annular layers for sustaining compressive loads, as shown in a longitudinal view in FIG. 2.

In adults, the intervertebral disc 100 is avascular. Survival of the disc cells depends on diffusion of nutrients from external blood vessels 112 and capillaries 107 through the cartilage 106 of the endplates 105, as shown in FIG. 2. Diffusion of nutrients also permeates from peripheral blood vessels adjacent to the outer annulus, but these nutrients can only permeate up to 1 cm into the annular layers of the disc 100. An adult disc can be as large as 5 cm in diameter; hence diffusion through the cranial and caudal endplates 105 is crucial for maintaining the health of the nucleus pulposus 128 and inner annular layers of the disc 100.

Calcium pyrophosphate and hydroxyapatite are commonly found in the endplate 105 and nucleus pulpous 128. As young as 18 years of age, calcified layers 108 begin to accumulate in the cartilaginous endplate 105, as shown in FIG. 3. The blood vessels 112 and capillaries 107 at the bone-cartilage interface are gradually occluded by the build-up of the calcified layers 108, which form into bone. Bone formation at the endplate 105 increases with age.

When the endplate 105 is obliterated by bone, diffusion between the nucleus pulposus 128 and blood vessels 112 beyond the endplate 105 is greatly limited. In addition to hindering the diffusion of nutrients, calcified endplates 105 further limit the permeation of oxygen into the disc 100. Oxygen concentration at the central part of the nucleus 128 is extremely low. Cellularity of the disc 100 is already low compared to most tissues. To obtain necessary nutrients and oxygen, cell activity is restricted to being on or in very close proximity to the cartilaginous endplate 105. Furthermore, oxygen concentrations are very sensitive to changes in cell density or consumption rate per cell.

The supply of sulfate into the nucleus pulposus 128 for biosynthesizing sulfated glycosaminoglycans is also restricted by the calcified endplates 105. As a result, the sulfated glycosaminoglycan concentration decreases, leading to lower water content and swelling pressure within the nucleus pulposus 128. During normal daily compressive loading on the spine, the reduced pressure within the nucleus pulposus 128 can no longer distribute the forces evenly along the circumference of the inner annulus to keep the lamellae bulging outward. As a result, the inner lamellae sag inward, while the outer annulus continues to bulge outward, causing delamination 114 of the annular layers, as shown in FIGS. 3 and 4.

The shear stresses causing annular delamination and bulging are highest at the posteriolateral portions adjacent to the neuroforamen 121. The nerve 194 is confined within the neuroforamen 142 between the disc and the facet joint 142, 143. Hence, the nerve 194 at the neuroforamen 121 is vulnerable to impingement by the bulging disc 100 or bone spurs.

When oxygen concentration in the disc falls below 0.25 kPa (1.9 mm Hg), production of lactic acid dramatically increases with increasing distance from the endplate 105. The pH within the disc 100 falls as lactic acid concentration increases. Lactic acid diffuses through micro-tears of annulus irritating the richly innervated posterior longitudinal ligament 195, facet joint and/or nerve root 194. Studies indicate that lumbar pain correlates well with high lactate levels and low pH. The mean pH of symptomatic discs was significantly lower than the mean pH of the normal discs. The acid concentration is three times higher in symptomatic discs than normal discs. In symptomatic discs with pH 6.65, the acid concentration within the disc is 5.6 times the plasma level. In some preoperative symptomatic discs, nerve roots 194 were found to be surrounded by dense fibrous scars and adhesions with remarkably low pH 5.7-6.30. The acid concentration within the disc was 50 times the plasma level.

Approximately 85% of patients with low back pain cannot be given a precise pathoanatomical diagnosis. This type of pain is generally classified under "non-specific pain". Back pain and sciatica can be recapitulated by maneuvers that do not affect the nerve root, such as intradiscal saline injection, discography, and compression of the posterior longitudinal ligaments. It is possible that some of the non-specific pain is caused by lactic acid irritation secreted from the disc. Injection into the disc can flush out the lactic acid. Maneuvering and compression can also drive out the irritating acid to produce non-specific pain. Currently, no intervention other than discectomy can halt the production of lactic acid.

The nucleus pulposus 128 is thought to function as "the air in a tire" to pressurize the disc 100. To support the load, the pressure effectively distributes the forces evenly along the circumference of the inner annulus and keeps the lamellae bulging outward. The process of disc degeneration begins with calcification of the endplates 105, which hinders diffusion of sulfate and oxygen into the nucleus pulposus 128. As a result, production of the water absorbing sulfated glycosaminoglycans is significantly reduced, and the water content within the nucleus decreases. The inner annular lamellae begin to sag inward, and the tension on collagen fibers within the annulus is lost. The degenerated disc 100 exhibits unstable movement, similar to a flat tire. Approximately 20-30% of low-back-pain patients have been diagnosed as having spinal segmental instability. The pain may originate from stress and increased load on the facet joints and/or surrounding ligaments. In addition, pH within the disc 100 becomes acidic from the anaerobic production of lactic acid, which irritates adjacent nerves and tissues.

Resilient straightening of a super elastically curved needle within a rigid needle is described in prior art DE 44 40 346 A1 by Andres Melzer filed on Nov. 14, 1994 and FR 2 586 183-A1 by Olivier Troisier filed on Aug. 19, 1985. The curved needles of these prior art are used to deliver liquid into soft tissue. In order to reach the intervertebral disc without an external incision, the lengths of the curved and rigid needles must be at least six inches (15.2 cm). There are multiple problems when attempting to puncture the calcified endplate as described in the prior art. Shape memory material for making the curved needle usually is elastic. Nickel-titanium alloy has Young's modulus approximately 83 GPa (austenite), 28-41 GPa (martensite). Even if the handles of both the curved and rigid needles are restricted from twisting, the long and elastically curved needle 101 is likely to twist within the lengthy rigid needle 220 during endplate 105 puncturing, as shown in FIGS. 54 and 55. As a result, direction of puncture is likely to be deflected and endplate 105 puncture would fail.

Furthermore, in the prior art, the sharp tips of their rigid needles are on the concave sides of the curved needles. When puncturing a relatively hard tissue, such as calcified endplates 105, the convex sides of the curved needles are unsupported and vulnerable to bending, resulting in failure to puncture through the calcified endplates 105. To minimize bending or twisting, the sizes of their curved and rigid needles are required to be large. By increasing the sizes of the curved 101 and rigid 220 needles, friction between the curved 101 and rigid 220 needles greatly increases, making deployment and retrieval of the curved needle 101 very difficult. In addition, a large opening created in the disc 100 by the large needles may cause herniation of the nucleus pulposus 128. Similarly, a large opening at the endplate 105 may cause Schmorl's nodes, leakage of nucleus pulpous 128 into the vertebral body 159.

In essence, the support from the distal end of the rigid needle 220 in FIGS. 62-67 of this invention is relevant to support puncturing of a relatively hard tissue, such as calcified endplate 105 with a small diameter needle 101. Furthermore, the non-round cross-sections of the curved 101 and rigid 220 needles in FIGS. 56-60 to prevent twisting are also relevant to ensure successful puncturing through the calcified endplate 105.

SUMMARY OF INVENTION

In this invention, conduits are delivered through the calcified endplates to re-establish the exchange of nutrients and waste between the disc and vertebral bodies. The conduit is delivered within an elastically curved needle. The curved needle is resiliently straightened within a rigid needle. The rigid needle punctures into a degenerating disc with calcified endplates. The elastically curved needle carrying the conduit is then deployed from the rigid needle to resume the curved configuration and puncture through the calcified endplate. By retrieving the curved needle back into the rigid needle while holding a plunger behind the conduit stationary, the conduit is deployed across the endplate to transport nutrients and waste between the disc and vertebra.

The puncturing device in this invention is designed to minimize twisting and friction between the curved and rigid needles. The device also provides support to the elastically curved needle to minimize bending during endplate puncturing. In addition, the device is designed to deliver at least one conduit at the endplate to bridge between the avascular intervertebral disc and the vertebral body for exchange of nutrients, oxygen, carbon dioxide, lactate and waste.

Nutrients and oxygen are abundantly supplied by peripheral blood vessels near the outer annulus. Conduits can also be deployed transverse the degenerating disc to draw nutrients from the outer annulus into the nucleus pulposus to halt disc degeneration.

After nutrient and waste exchange is re-established by the semi-permeable conduits, stem cells, growth factor or gene therapeutic agents can be injected into the disc to promote regeneration. In addition, the disc with semi-permeable conduits is still immunoisolated. Donor cells injected into the disc can be nourished by nutrients through the semi-permeable conduits without triggering an immune response. These cells are selected for their capability to biosynthesize therapeutic agents, such as insulin and neurotransmitters. The therapeutic agents are transported through the semi-permeable conduits into body circulation to treat a disease.

| | |
|---|---|
| 100 | Intervertebral disc |
| 101 | Needle |
| 102 | Bevel or tapering |
| 103 | Trocar |
| 104 | Lumen or channel of conduit |
| 105 | Endplate |
| 106 | Hyaline cartilage |
| 107 | Capillaries |
| 108 | Blockade or calcified layers |
| 109 | Plunger |
| 110 | Monofilament |
| 112 | Blood vessels |
| 113 | Tissue gripping flange |
| 114 | Annular delamination |
| 115 | Epiphysis |
| 116 | Penetration marker |
| 121 | Neuroforamen |
| 122 | Braided multi-filament |
| 123 | Spinal cord |
| 124 | Porous conduit |
| 125 | Tube |
| 126 | Conduit |
| 127 | Electronic cutter or laser |
| 128 | Nucleus pulposus |
| 129 | Facet joint |
| 130 | Handle of curve needle |
| 131 | Guide rail of curve needle handle |
| 132 | Handle of rigid sleeve |
| 133 | Track of rigid sleeve handle |
| 134 | Electronic cutting device |
| 135 | Electric cord |
| 140 | Sacrum |
| 142 | Superior articular process |
| 143 | Inferior articular process |
| 153 | Label indicating curved direction |
| 159 | Vertebral body |
| 160 | Tissue ingrowth indentation |
| 161 | Knot |
| 162 | Protrusion or ring |
| 163 | Coating |
| 184 | Impingement |
| 193 | Psoas muscle |
| 194 | Nerve root |
| 195 | Posterior longitudinal ligament |
| 121 | Neuroforamen |
| 217 | Screw entry |
| 220 | Rigid sleeve or needle |
| 224 | Puncture |
| 230 | Dilator |

-continued

| | |
|---|---|
| 268 | Lumen of rigid sleeve |
| 269 | Lumen of rigid needle |
| 270 | Window of rigid sleeve |
| 271 | Shape memory extension |
| 272 | Ramp in lumen of rigid needle |
| 276 | Syringe |
| 277 | Donor cells |

BRIEF DESCRIPTION OF THE DRAWINGS

FIG. 9 depicts an elastically curved needle 101.

FIG. 10 shows the elastic needle 101 being resiliently straightened within a rigid sleeve 220.

FIG. 11 shows a round cross-section of the needle 101 within the rigid sleeve 220.

FIG. 20 shows insertion of the elastic tube 125 onto the elastically curved needle 101 with a sliding plunger 109 abutting the tube 125.

FIG. 21 depicts the needle 101 carrying the elastic tube 125 being resiliently straightened within the rigid sleeve 220.

FIG. 22 shows insertion of the needle 101, elastic tube 125, sleeve 220 and plunger 109 into the dilator 230.

FIG. 23 depicts deployment of the needle 101 delivering the tube 125 through the calcified layer 108 of the endplate 105.

FIG. 29 depicts the assembly with the rails 131 in the tracks 133 to avoid rotation between the needle 101 and the sleeve 220.

FIG. 30 shows resumption of the curvature as the elastically curved needle 101 is deployed from the rigid sleeve 220.

FIG. 54 depicts twisting of the curved needle 101 within the rigid sleeve 220 during endplate 105 puncturing. The cross-section is shown in FIG. 62.

FIG. 55 shows the cross-sectional view of FIG. 61. The elastic needle 101 twists or rotates within the rigid sleeve 220.

FIG. 56 depicts prevention of twisting by using a needle 101 and sleeve 220 with elliptical cross-sections.

FIG. 57 shows a cross-sectional view of the elliptical needle 101 within the elliptical sleeve 220, depicted in FIG. 63, to limit rotational movement.

FIG. 58 indicates a square cross-section of the needle 101 and sleeve 220.

FIG. 59 indicates a rectangular cross-section of the needle 101 and sleeve 220.

FIG. 60 indicates a triangular cross-section of the needle 101 and sleeve 220.

FIG. 68 depicts the elastically curved needle 101 within a curved shape memory extension 271. Both curved needle 101 and extension 271 are housed within a rigid sleeve 220.

FIG. 69 shows resilient straightening of the shape memory extension 271 within the rigid sleeve 220.

FIG. 70 shows endplate 105 puncturing by the fortified curved needle 101 without increasing the size of the endplate 105 puncture.

FIG. 71 shows a sharpened shape memory extension 271 to support endplate 105 puncturing.

FIG. 81 depicts a radiopaque, echogenic or magnetic coating 163 on the needle 101 to indicate the location of the conduit 126 within the needle 101.

FIG. 82 shows two conduits 126 inserted through the disc 100 to exchange nutrients and waste between the outer annulus and the nucleus pulposus 128.

FIG. 83 depicts the distal tip of the needle 101 penetrating beyond the intervertebral disc 100.

DETAILED DESCRIPTION OF THE EMBODIMENTS

Figure 1:
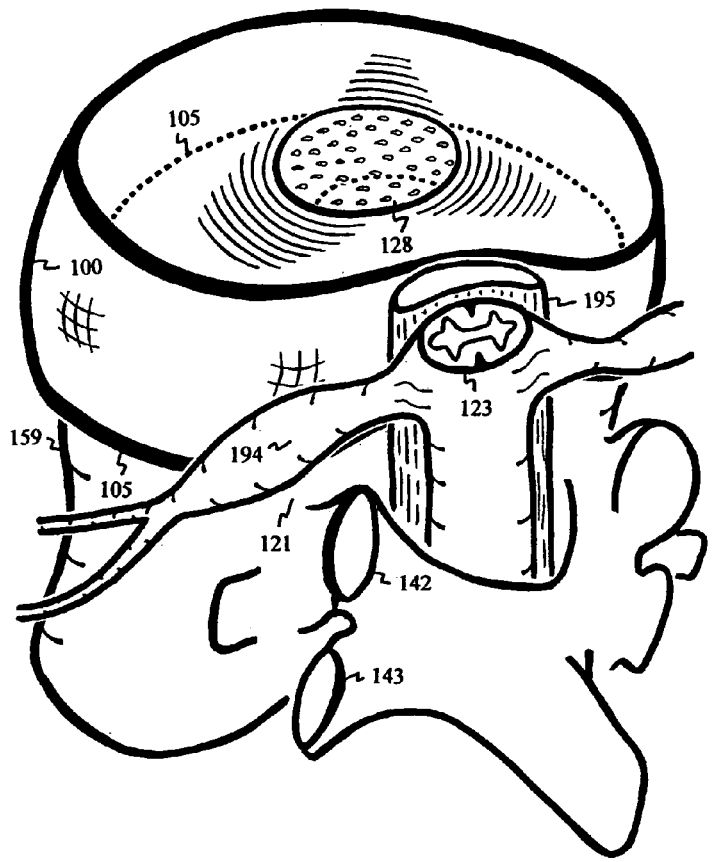
FIG. 1 depicts a healthy disc 100 with normal swelling pressure within the nucleus pulposus 128 to support the layers of annulus during compressive loading.
Figure 2:
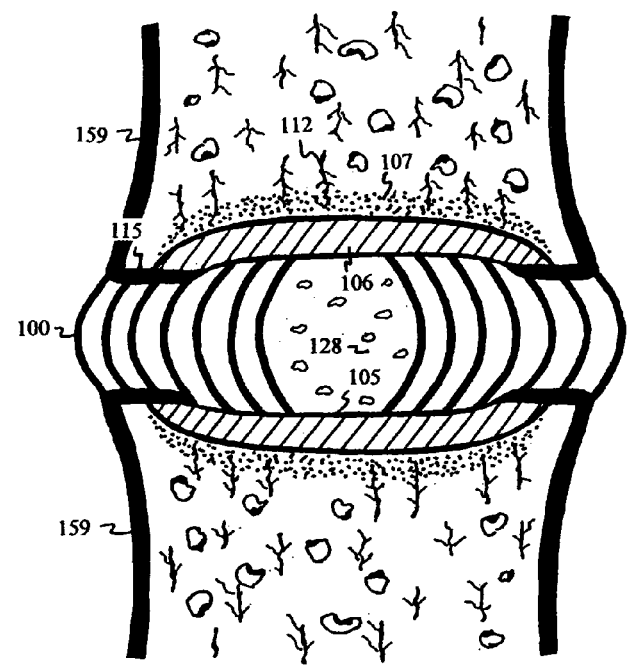
FIG. 2 shows a longitudinal view of a spine segment, displaying outward bulging of annular layers during compression of a healthy disc 100 between cartilaginous 106 endplates 105.
Figure 3:
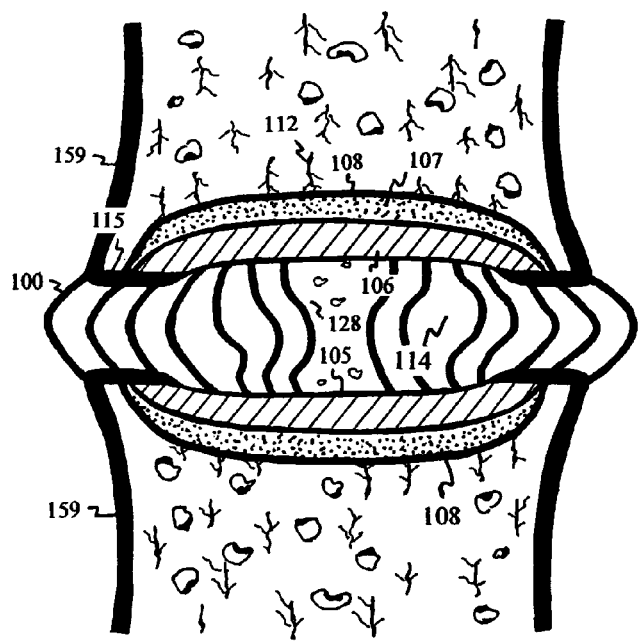
FIG. 3 shows that the calcified layers 108 of the endplates 105 hinder diffusion of nutrients between the inner disc 100 and the vertebral bodies 159, leading to inward bulging and annular delamination 114.
Figure 4:
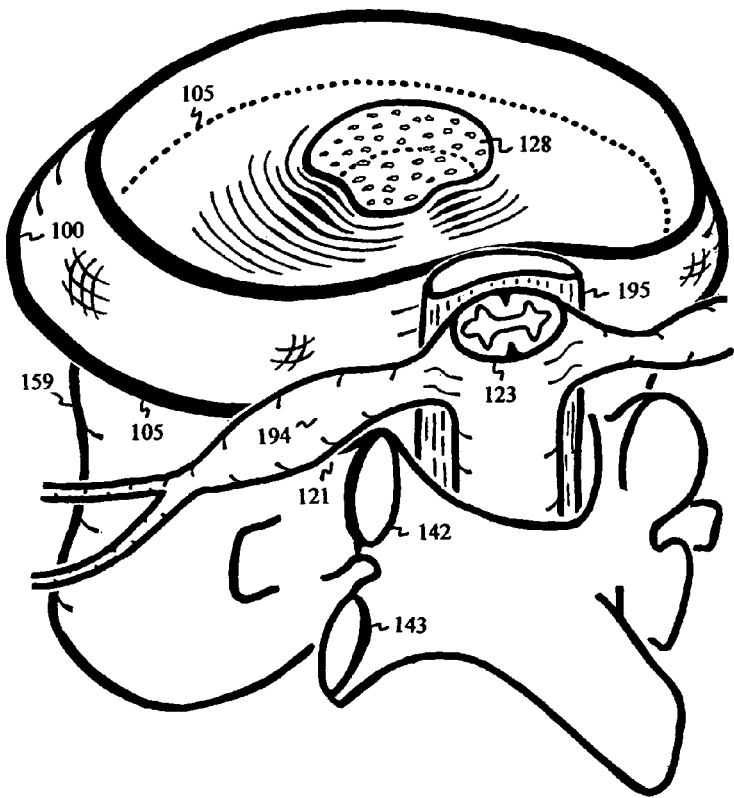
FIG. 4 depicts a degenerated and flattened disc with reduced swelling pressure within the nucleus pulposus 128 and annular delamination.
Figure 5:
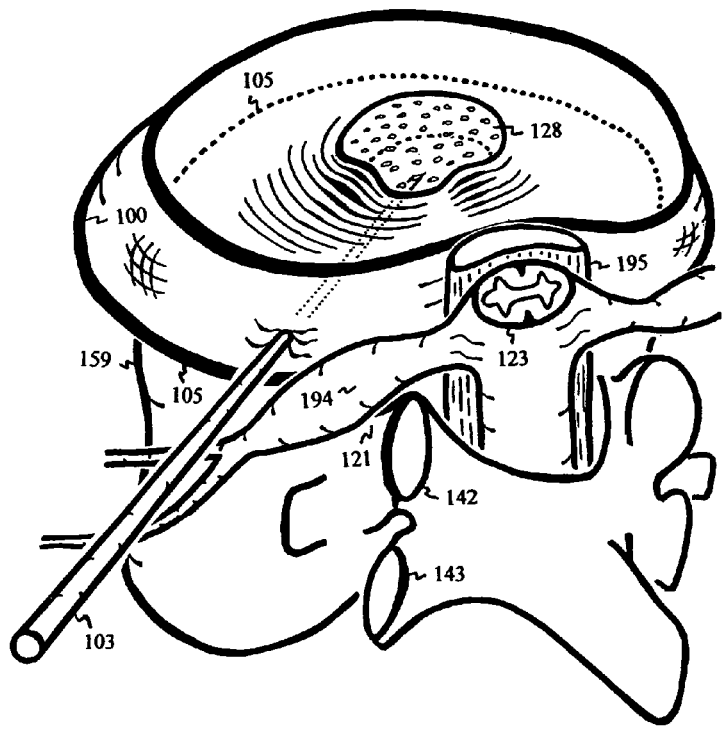
FIG. 5 depicts trocar 103 insertion into the disc 100 using the guiding technique similar to that used in discography.
Figure 6:
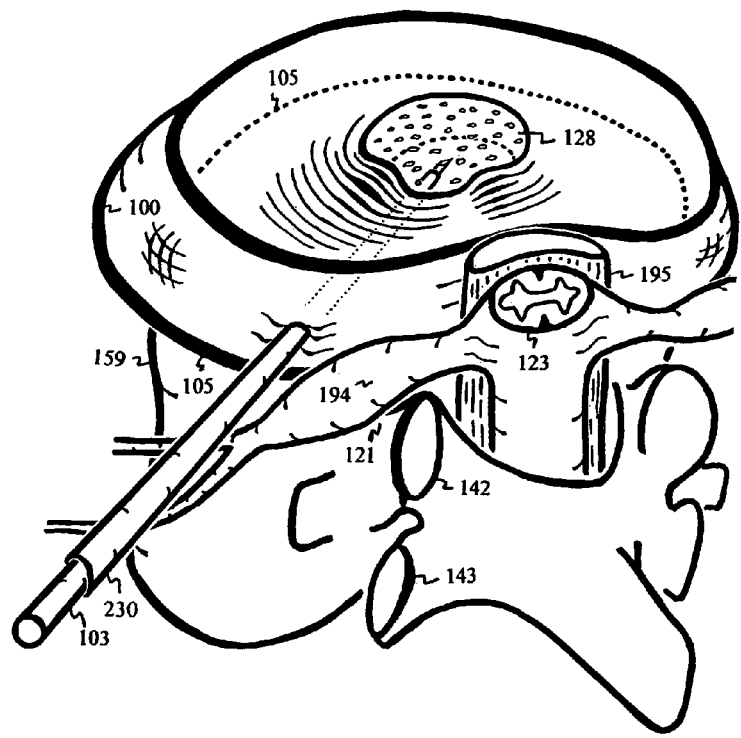
FIG. 6 shows insertion of a dilator 230 over the trocar 103.
Figure 7:
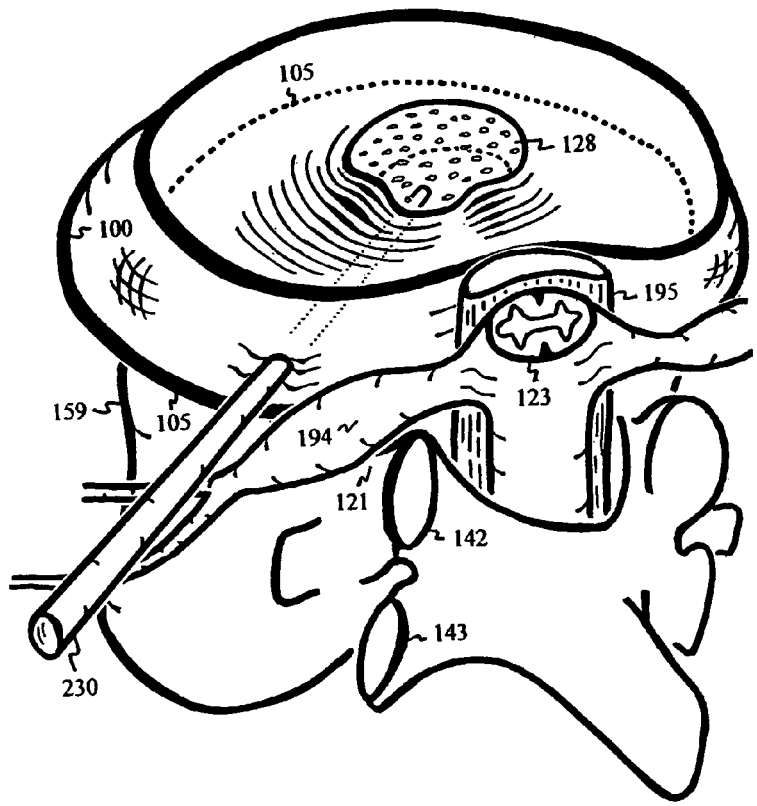
FIG. 7 depicts withdrawal of the trocar 103. The dilator 230 acts as a passage leading into the disc 100.
Figure 8:
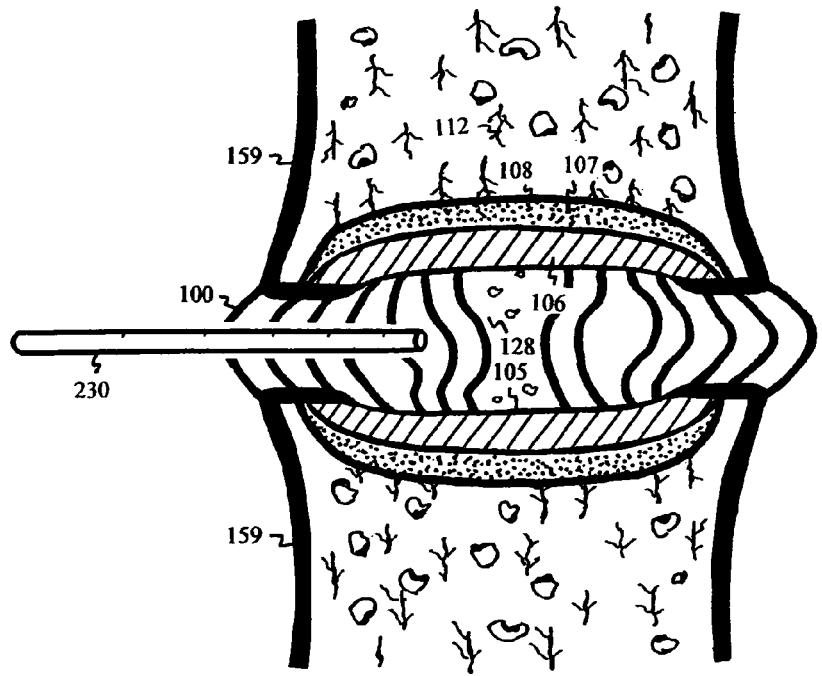
FIG. 8 shows a longitudinal view of the degenerated spinal segment with insertion of the dilator 230.

Since diffusion from the endplate 105 is crucial for maintaining the intervertebral disc, effort is made to re-establish nutrient and waste exchange between the nucleus pulposus and circulation within the vertebral body. Guided by anteroposterior and lateral views from fluoroscopes, a trocar 103 enters posteriolaterally, 45° from mid-line into the disc 100, as shown in FIG. 5. This guiding technique is similar to the one used in diagnostic injection of radiopaque dye for discography or chymopapain injection for nucleus pulposus digestion. A dilator 230 is inserted over the trocar 103, as shown in FIG. 6. The trocar 103 is then withdrawn. The dilator 230 remains as a passage leading into the disc 100, as shown in FIG. 7. FIG. 8 shows the distal end of the dilator 230 near the nucleus pulposus 128 of the degenerating disc 100.

Figure 12:
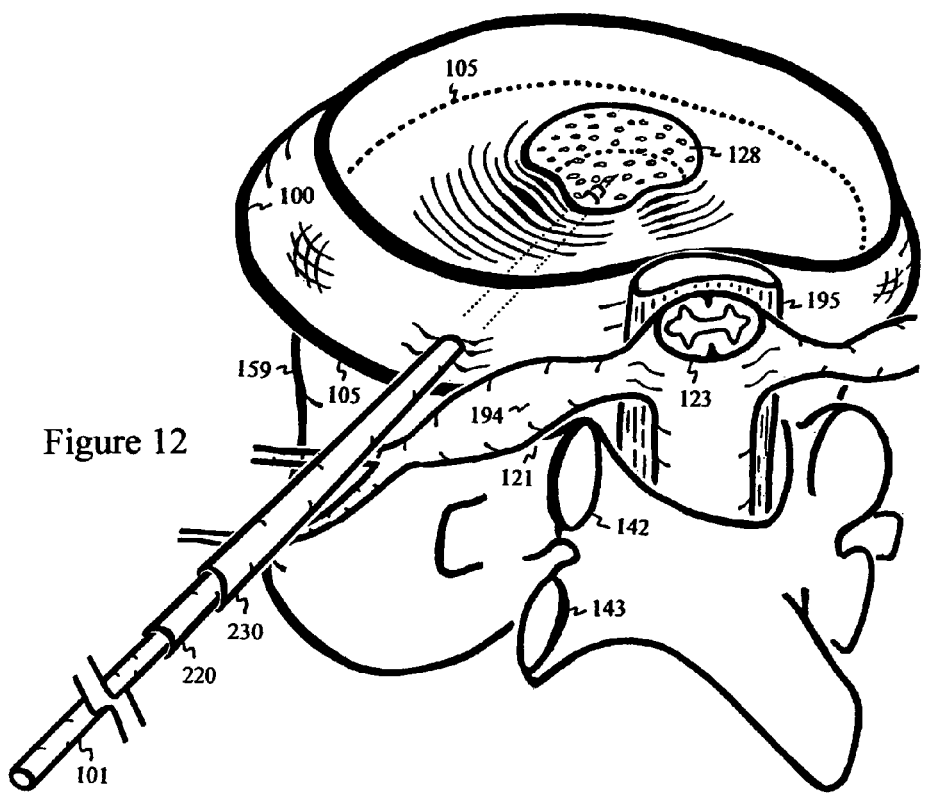
FIG. 12 depicts insertion of the resiliently straightened needle 101 within the rigid sleeve 220 into the dilator 230 leading into the disc 100.
Figure 13:
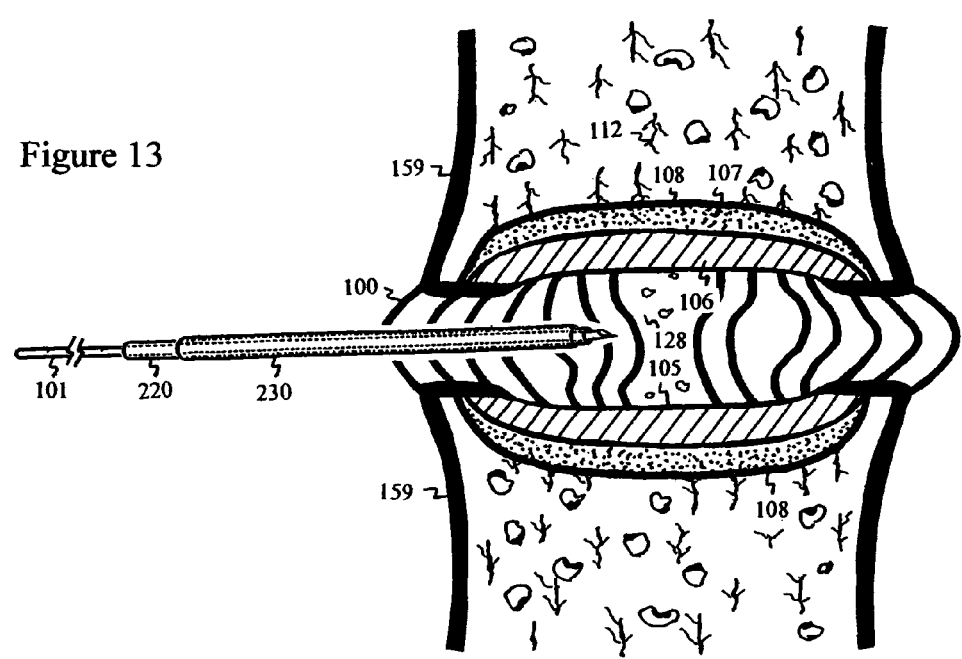
FIG. 13 shows a longitudinal view of the needle 101 and sleeve 220 assembly inserted into the dilator 230 leading into the disc 100.
Figure 14:
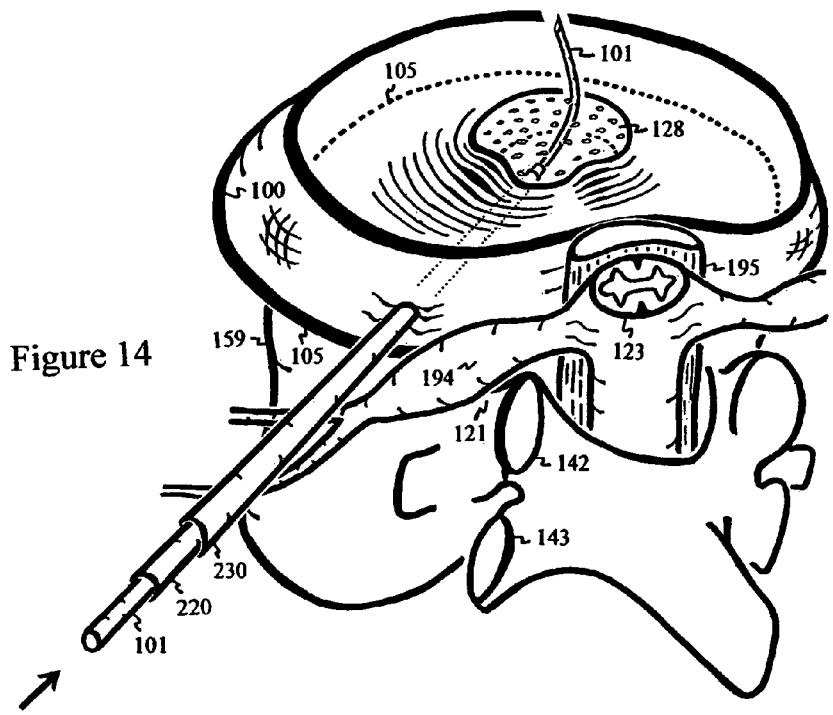
FIG. 14 depicts upward puncturing of the needle 101 into the endplate 105 (not shown) by deploying the resiliently straightened needle 101 from the rigid sleeve 220.
Figure 15:
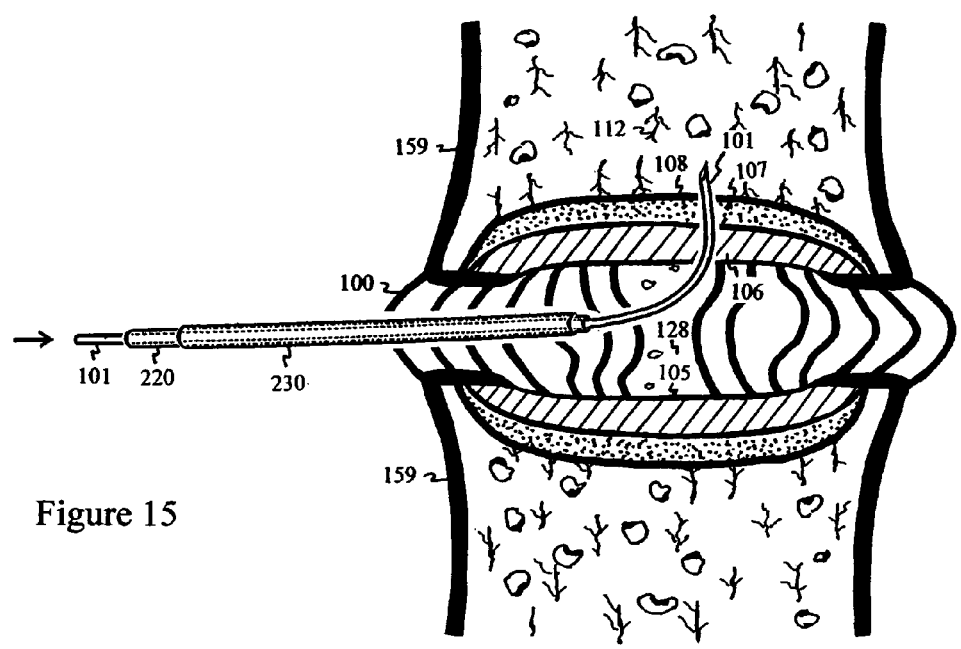
FIG. 15 shows endplate 105 puncturing through the calcified layers 108 by deploying the curved needle 101 from the rigid sleeve 220.

An elastically curved needle 101, as shown in FIG. 9, is resiliently straightened in a rigid sleeve 220 indicated in FIG. 10. The round cross section of the straightened needle 101 and sleeve 220 is shown in FIG. 11. The resiliently straightened needle 101 within the rigid sleeve 220 is inserted into the dilator 230 and the disc 100, as shown in FIG. 12. A longitudinal view of the needle 101 insertion into the degenerating disc 100 is indicated in FIG. 13. The elastically curved needle 101 is deployed by holding the rigid sleeve 220 stationary while pushing the needle 101 inward. The needle 101 resumes the curved configuration as it exits the distal opening of the sleeve 220, puncturing upward as shown in FIG. 14, through the cartilage 106 and calcified layers 108 into the vertebral body 159, as indicated in FIG. 15.

Figure 16:
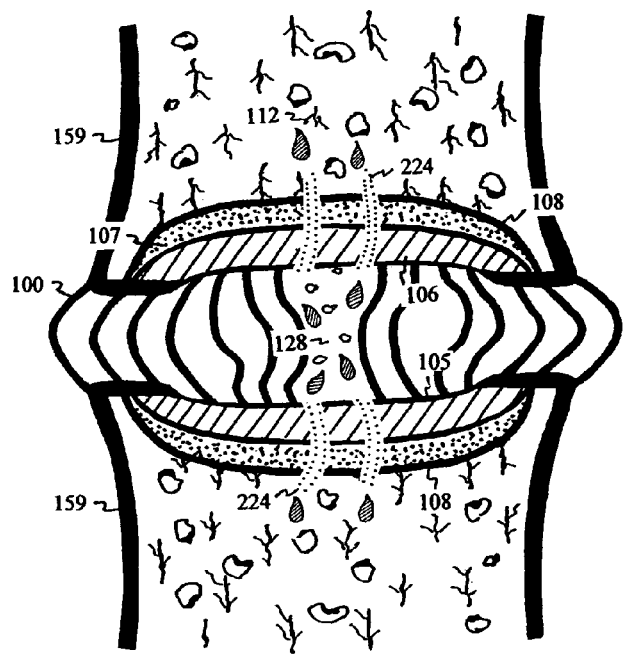
FIG. 16 depicts permeation of water, nutrients and metabolites through the puncture sites 224 of the superior and inferior endplates 105.
Figure 17:
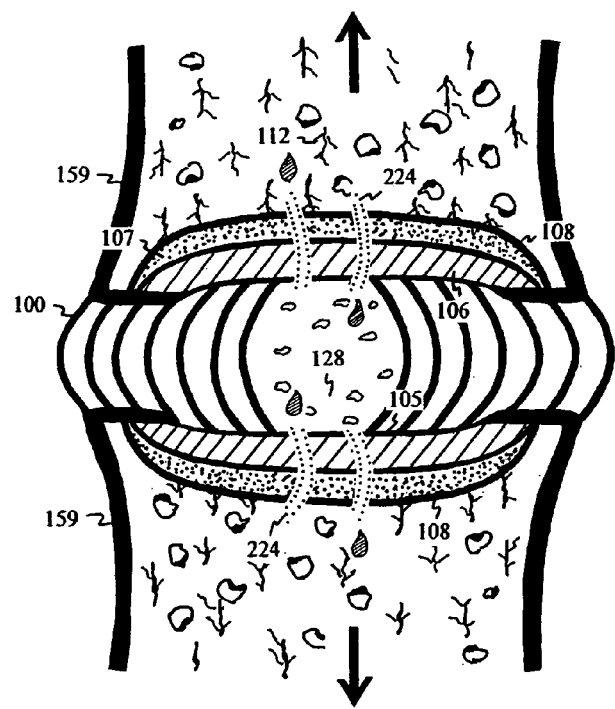
FIG. 17 depicts re-establishment of swelling pressure by the renewed biosynthesis of glycosaminoglycan within the nucleus pulposus 128.

Multiple endplate 105 punctures 224 can be accomplished to re-establish the exchange of nutrients and waste between the disc 100 and bodily circulation. After retrieving the elastically curved needle 101 into the sleeve 220, the assembly of needle 101 and sleeve 220 can be further advanced into or slightly withdrawn from the disc 100 to puncture more holes 224 through the calcified cranial endplate 105. By turning the assembly of needle 101 and sleeve 220 180°, the caudal endplate 105 can also be punctured, as shown in FIG. 16, to re-establish the exchange of nutrients, oxygen and waste through the superior and inferior endplates 105. FIG. 17 indicates restoration of swelling pressure within the nucleus pulposus 128 enabling the disc 100 to sustain compressive loads. With the presence of oxygen within the disc 100, production of lactic acid may also decrease and ease chemical irritation and pain.

Figure 18:
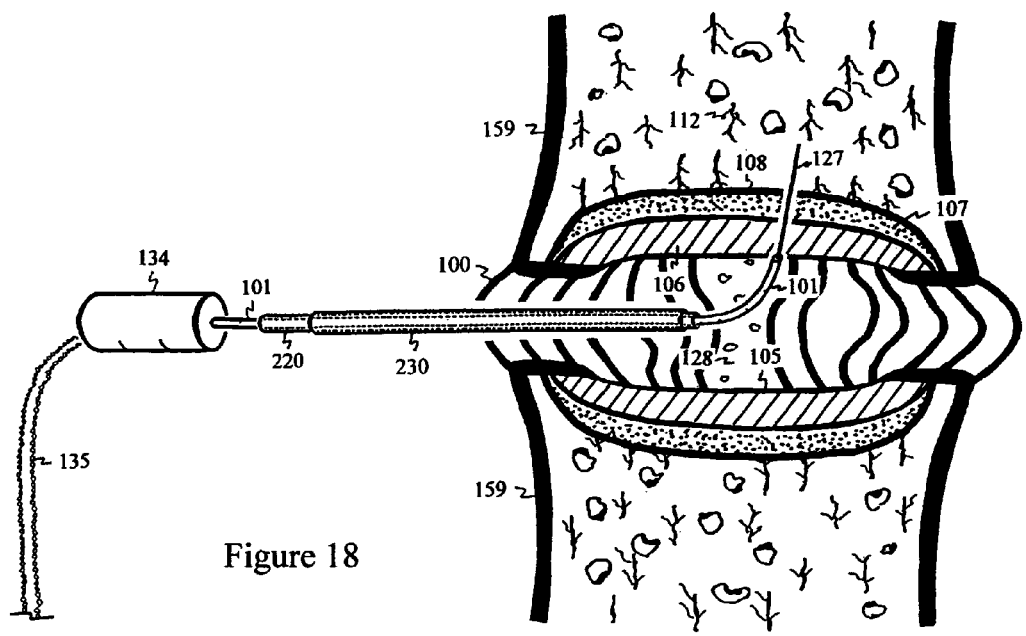
FIG. 18 depicts an electronic device 134 empowering a cutter 127 to puncture, drill, abrade or cauterize through the calcified endplate 105.

Endplate 105 puncturing can also be accomplished by electronic devices 134, such as a laser, cutting or abrading device. FIG. 18 depicts an electronic device 134 powering a cutter 127 to puncture, drill, abrade or cauterize the endplate 105 to re-establish the exchange of nutrients and waste. The electronic device 134 can be a cautery, laser, or drill.

Figure 19:
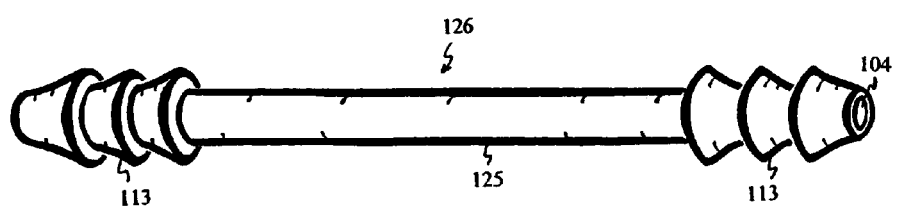
FIG. 19 depicts a conduit 126 in the form of an elastic tube 125 with tissue-holding flanges 113 and longitudinal opening 104.
Figure 24:
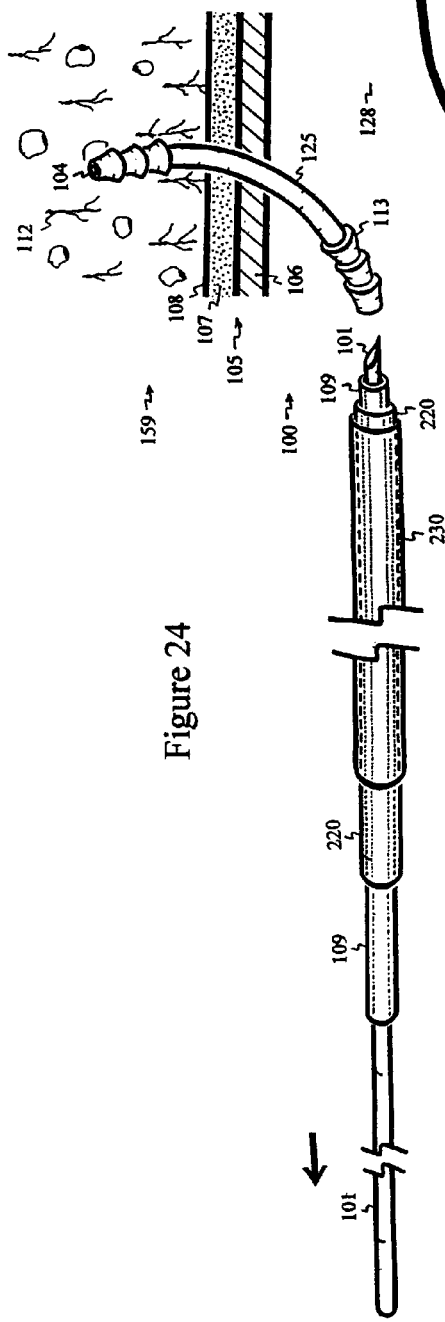
FIG. 24 shows withdrawal of the needle 101 while holding the plunger 109 stationary to dislodge the tube 125 from the needle 101.
Figure 25:
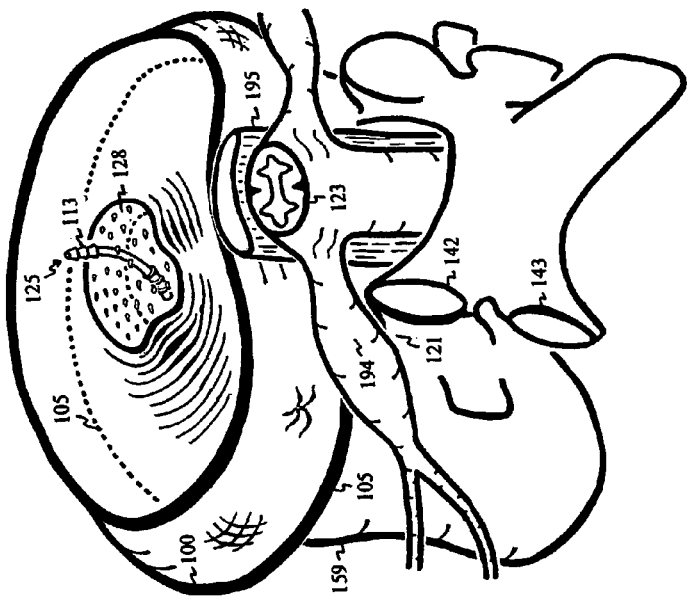
FIG. 25 shows the lower portion of the tube 125 dislodged within the nucleus pulposus 128 and the top portion deployed within the cranial vertebral body 159 (not shown) through the endplate 105 (also not shown).

Re-establishing the exchange of nutrients and waste through the calcified endplate 105 can also be accomplished using a conduit 126. A conduit 126 can be an elastic tube 125 with a lumen or channel 104 and tissue-holding flanges 113 at both ends, as shown in FIG. 19. The orientations of the flanges 113 located at both ends of the conduit 126 are counter gripping to anchor onto the endplate 105. The tube 125 is inserted over the elastically curved needle 101 and abutting a sliding plunger 109, as shown in FIG. 20. The needle 101 carrying the elastic tube 125 is resiliently straightened within the rigid sleeve 220, as depicted in FIG. 21. The assembly of the straightened needle 101, tube 125, sleeve 220 and plunger 109 is inserted into the dilator 230, as shown in FIG. 22, and into the disc 100. As the resilient needle 101 carrying the tube 125 is deployed from the rigid sleeve 220, the curvature of the needle 101 resumes and punctures through the calcified endplate 105, as shown in FIG. 23. The needle 101 is withdrawn while the plunger 109 is held stationary to dislodge the tube 125 from the needle 101 into the endplate 105, as shown in FIG. 24. The lumen 104 of the tube 125 acts as a passage for exchanging nutrients, gases and waste between the vertebral body 159 and the inner disc 100. A portion of the tube 125 is in the nucleus pulposus 128 or inner disc 100, while the remaining portion is within the vertebral body (not shown) in FIG. 25.

Figure 26:
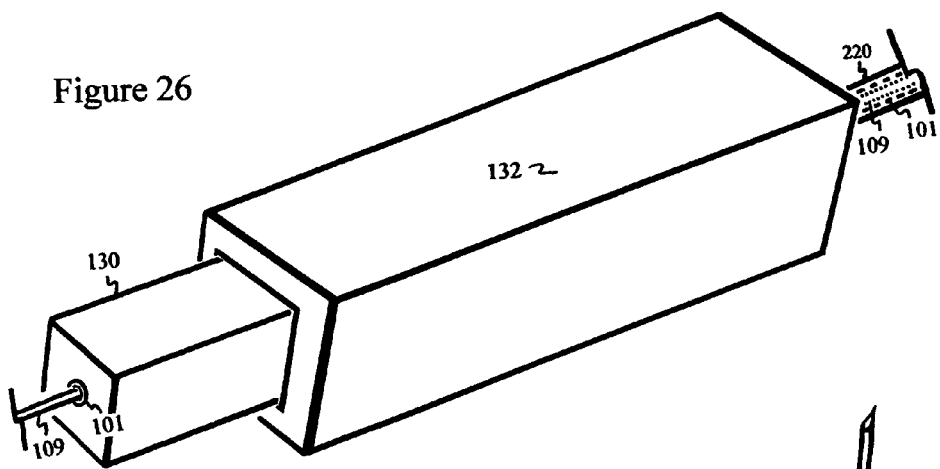
FIG. 26 depicts stacking of a square handle 130 of the curved needle 101 within a handle 132 of the rigid sleeve 220 to avoid rotation between the needle 101 and sleeve 220.
Figure 27:
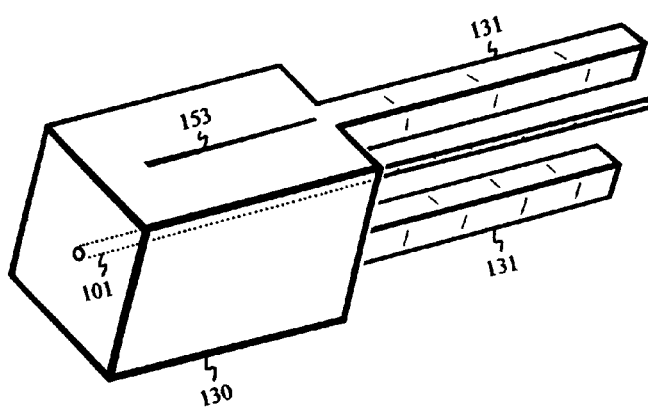
FIG. 27 depicts a handle 130 of the elastically curved needle 101, containing guide rails 131 and an orientation line 153 to show the direction of the curvature.
Figure 28:
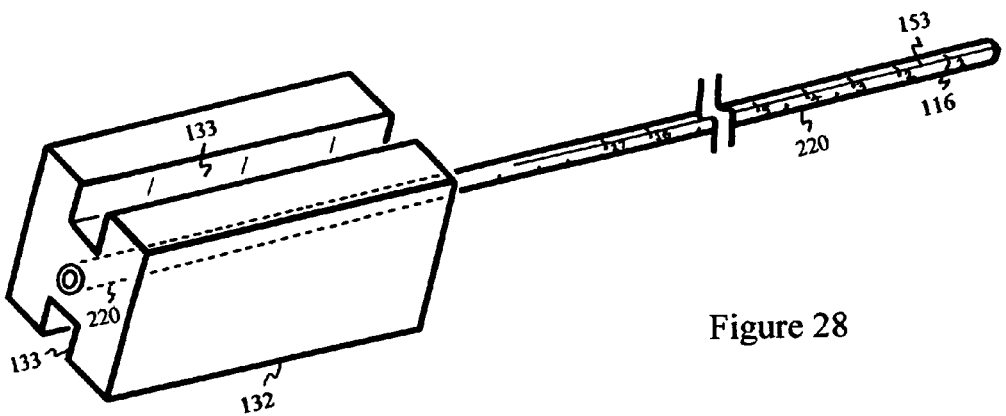
FIG. 28 shows tracks 133 on a handle 132 of the rigid sleeve 220 with orientation line 153 and penetration markers 116.

The handle 130 of the curved needle 101 and the handle 132 of the rigid sleeve 229 are used to maintain the direction of needle 101 deployment. The square handle 130 of the curved needle 101 is stacked within the handle 132 of the rigid sleeve 220, as shown in FIG. 26, to avoid rotation between the needle 101 and sleeve 220. The handle 130 of the needle 101 can also contain guide rails 131, as shown in FIG. 27. The guide rails 131 are sized and configured to fit within the sunken tracks 133 on the handle 132 of the rigid sleeve 220, as indicated in FIG. 28. Direction of the needle's curvature is indicated by the orientation lines 153 on the handle 130 of the needle 101, as shown in FIG. 27, and on the rigid sleeve 220 as shown in FIG. 28. To indicate depth of insertion into the body, penetration markers 116 are labeled on the sleeve 220, as shown in FIG. 28. The guide rails 131 within the tracks 133 keep the handles 130, 132 from rotating around each other, as shown in FIG. 29. As the resiliently straightened needle 101 advances and protrudes from the rigid sleeve 220, the curvature of the needle 101 resumes, as shown in FIG. 30. Since the handle 130 of the needle 101 and the handle 132 of the sleeve 220 are guided by the rails 131 in tracks 133, the direction of needle 101 puncturing is established and predictable for the operator or surgeon.

Figure 31:
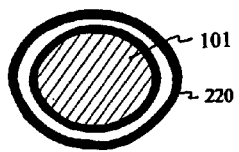
FIG. 31 shows oval cross-sections of the needle 101 and the rigid sleeve 220 to prevent rotation between the needle 101 and sleeve 220.
Figure 32:
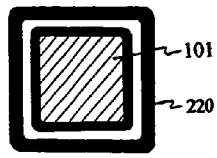
FIG. 32 indicates square cross-sections of the needle 101 within the sleeve 220.
Figure 33:
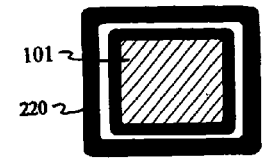
FIG. 33 depicts rectangular cross-sections of the needle 101 within the sleeve 220.
Figure 34:
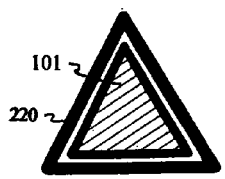
FIG. 34 shows triangular cross-sections of the needle 101 within the sleeve 220.

Non-circular cross-sections of the needle 101 and rigid sleeve 220 can also prevent rotation. FIG. 31 shows a needle 101 and a sleeve 220 with oval cross-section. FIG. 32 indicates a square cross-section. FIG. 33 depicts a rectangular cross-section. FIG. 34 shows a triangular cross-section.

Figure 35:
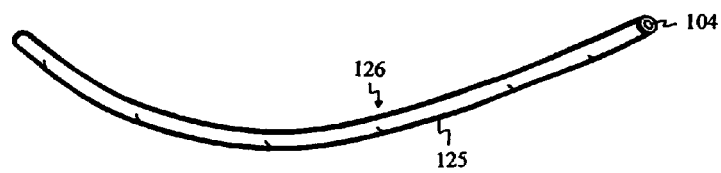
FIG. 35 depicts a conduit 126 made as a small tube 125 with a longitudinal channel 104.
Figure 36:
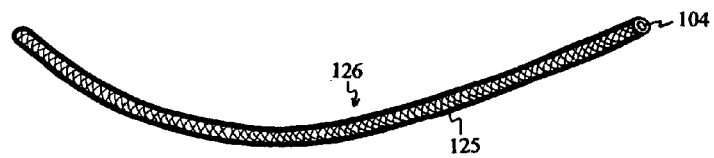
FIG. 36 indicates a conduit 126 made as a braided tube 125 with a longitudinal channel 104.
Figure 37:
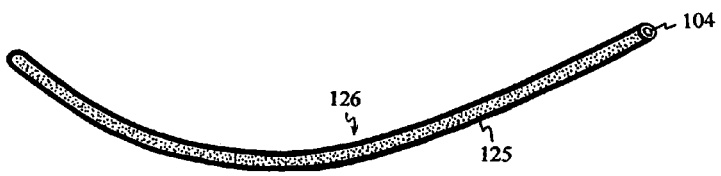
FIG. 37 shows a conduit 126 made with porous material in a tubular form 125.

Conduits 126 can also be made small enough to fit within the lumen of the elastically curved needle 101. A conduit 126 can be a small tube 125 with a longitudinal channel 104, as shown in FIG. 35, for transporting nutrients, oxygen and waste dissolved in fluid. The tubular conduit 126 with a lumen 104 can be braided or weaved with filaments, as shown in FIG. 36. The fluid can be transported through the lumen 104 as well as permeated through the braided filaments of the tube 125. The tubular conduit 126 can also be molded or extruded with porous or spongy material, as shown in FIG. 37, to transport nutrients, oxygen and waste dissolved in fluid through the lumen 104 as well as through the pores.

Figure 38:
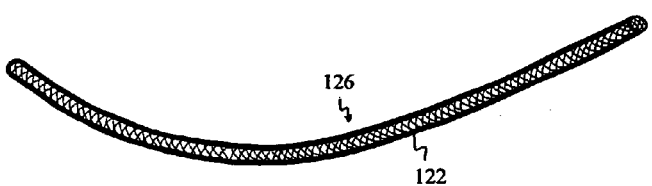
FIG. 38 depicts a conduit 126 made as a braided suture 122 or braided thread 122.
Figure 39:
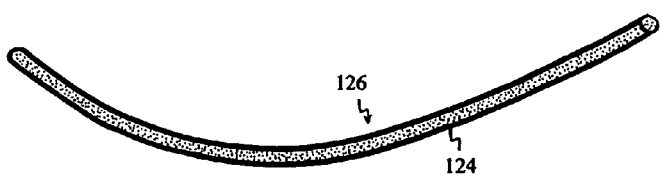
FIG. 39 indicates a conduit 126 made with a flexible porous or spongy fiber 124.

Nutrients, oxygen, lactate, metabolites, carbon dioxide and waste can also be transported in fluid through capillary action of multi-filaments or braided filaments 122, as shown in FIG. 38. A conduit 126 may not require the longitudinal lumen 104 as mentioned. A strand of braided filaments 122 can be a suture with channels formed among weavings of the filaments, capable of transporting fluid with nutrients, gases and waste. The braided filaments 122 can be coated with a stiffening agent, such as starch, to aid deployment using the plunger 109. Similar to the channels formed by the braided filaments 122, a conduit 126 made as a spongy thread 124, as shown in FIG. 39, can also transport fluid with nutrients, gases and wastes through the pores and channels formed within the porous structure.

Figure 41:
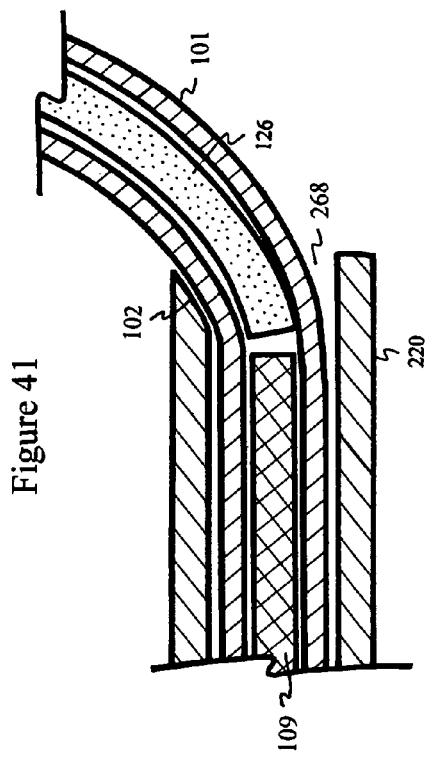
FIG. 41 shows a bevel 102 at the distal end of the lumen 268 of the rigid sleeve 220 to minimize friction during deployment and retrieval of the curved needle 101.
Figure 40:
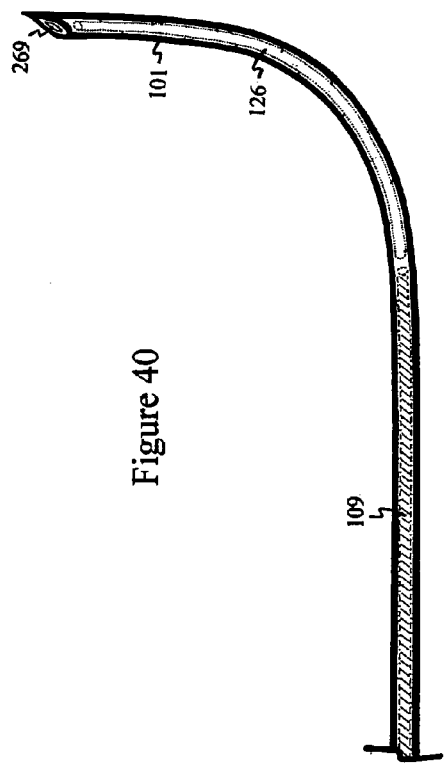
FIG. 40 shows a conduit 126 abutting against a plunger 109 within a lumen 269 of an elastically curved needle 101.
Figure 42:
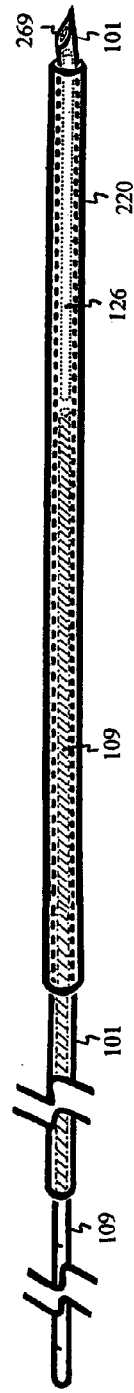
FIG. 42 depicts the elastically curved needle 101 with the conduit 126 being resiliently straightened within a rigid sleeve 220.
Figure 43:
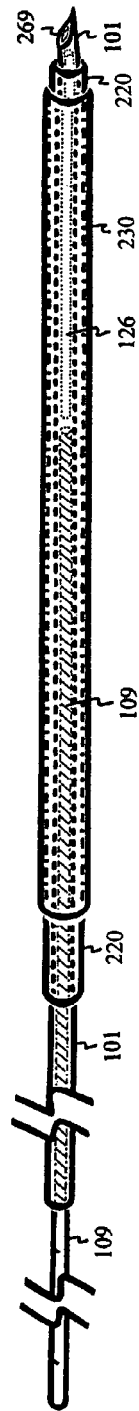
FIG. 43 indicates insertion of the assembly containing the needle 101, conduit 126, plunger 109 and sleeve 220 into a dilator 230.
Figure 44:
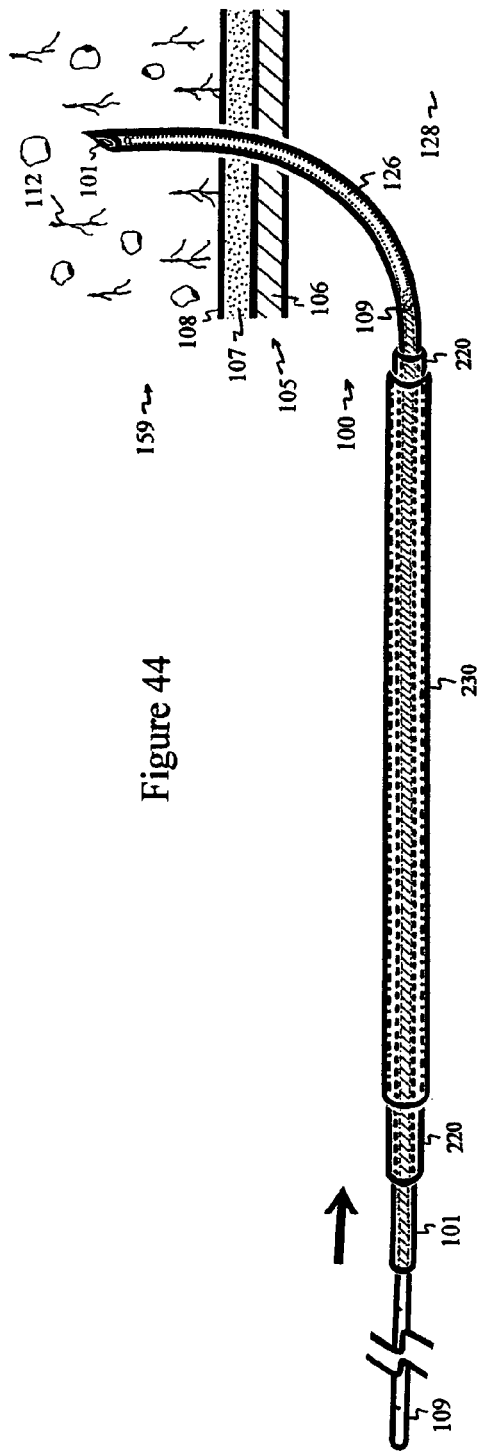
FIG. 44 shows deployment of the curved needle 101 through the calcified endplate 105.
Figure 45:
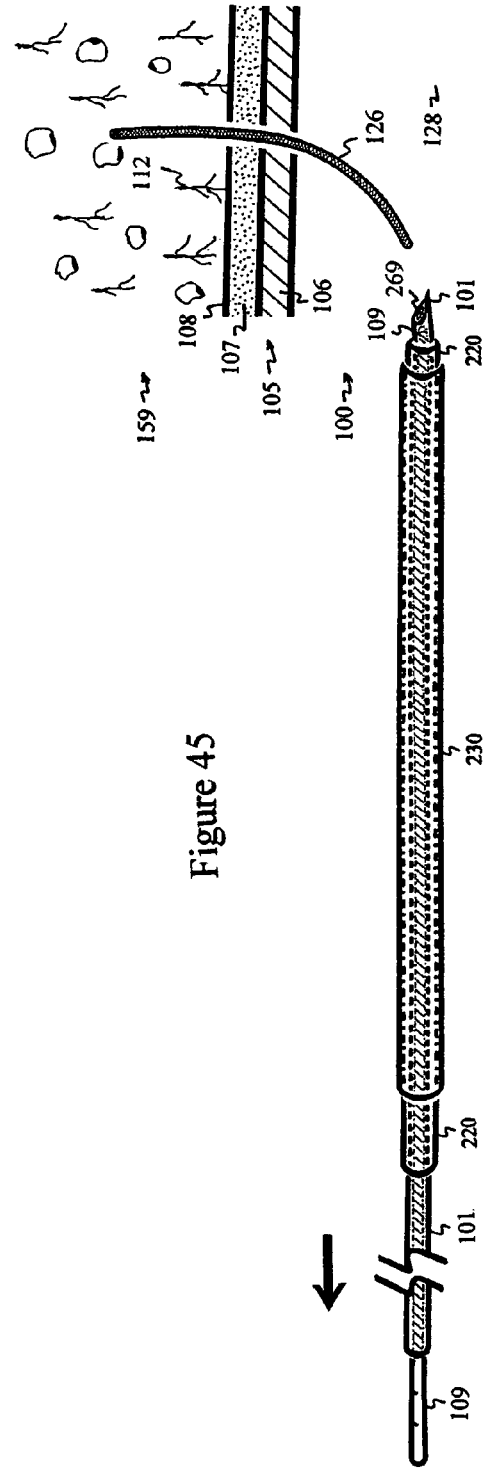
FIG. 45 depicts dislodgement of the conduit 126 by withdrawing the needle 101 while holding the plunger 109 stationary.

A conduit 126 is inserted into a longitudinal opening 269 of an elastically curved needle 101 abutting a plunger 109, as shown in FIG. 40. To minimize friction between the curved needle 101 and the rigid sleeve 220, the distal end of the lumen 268 of the sleeve 220 is angled or tapered with a bevel 102 or an indentation, conforming to the concave curvature of the needle 101, as shown in FIG. 41. A lubricant or coating to lower friction can also be applied on the surface of the elastically curved needle 101 and/or within the lumen 268 of the rigid sleeve 220. The elastically curved needle 101 carrying the conduit 126 is resiliently straightened within a rigid sleeve 220, as shown in FIG. 42. The assembly is then inserted into a dilator 230, as indicated in FIG. 43, which leads into the disc 100. As the resiliently straightened needle 101 is deployed from the sleeve 220, the needle 101 carrying the conduit 126 resumes the curved configuration and punctures into the cartilaginous endplate 105 through the calcified layers 108, as shown in FIG. 44. The elastically curved needle 101 is then retrieved into the sleeve 220 while the plunger 109 is held stationary to deploy the conduit 126 at the calcified endplate 105, as shown in FIG. 45.

Figure 46:
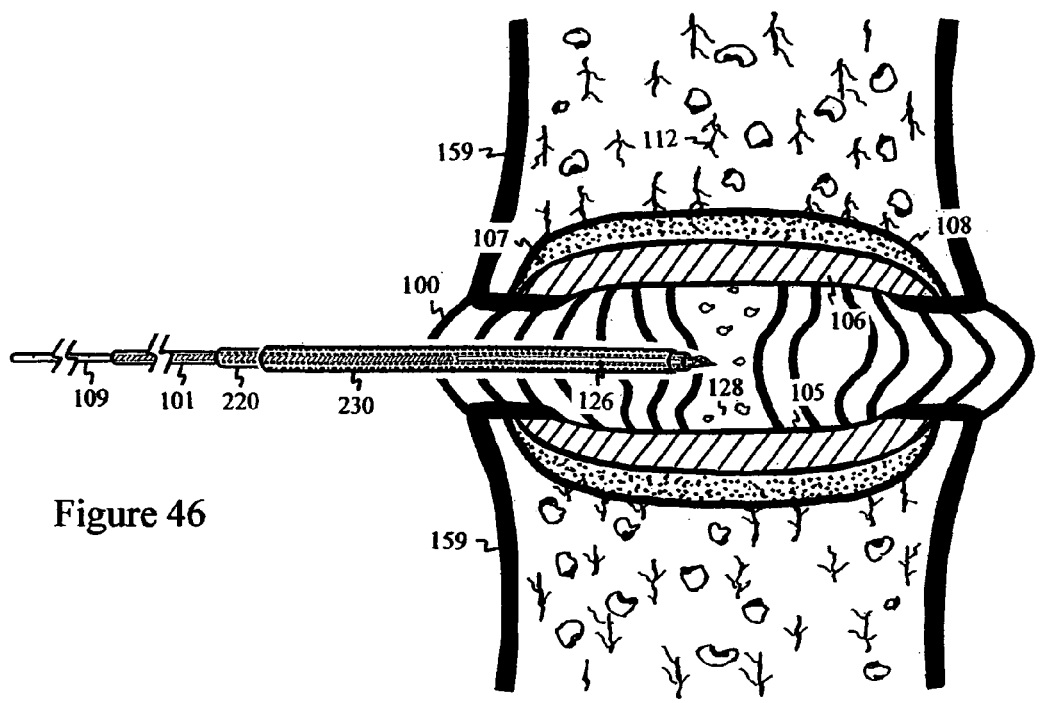
FIG. 46 depicts insertion of the needle 101, conduit 126, plunger 109 and sleeve 220 assembly into the dilator 230 leading into disc 100.
Figure 47:
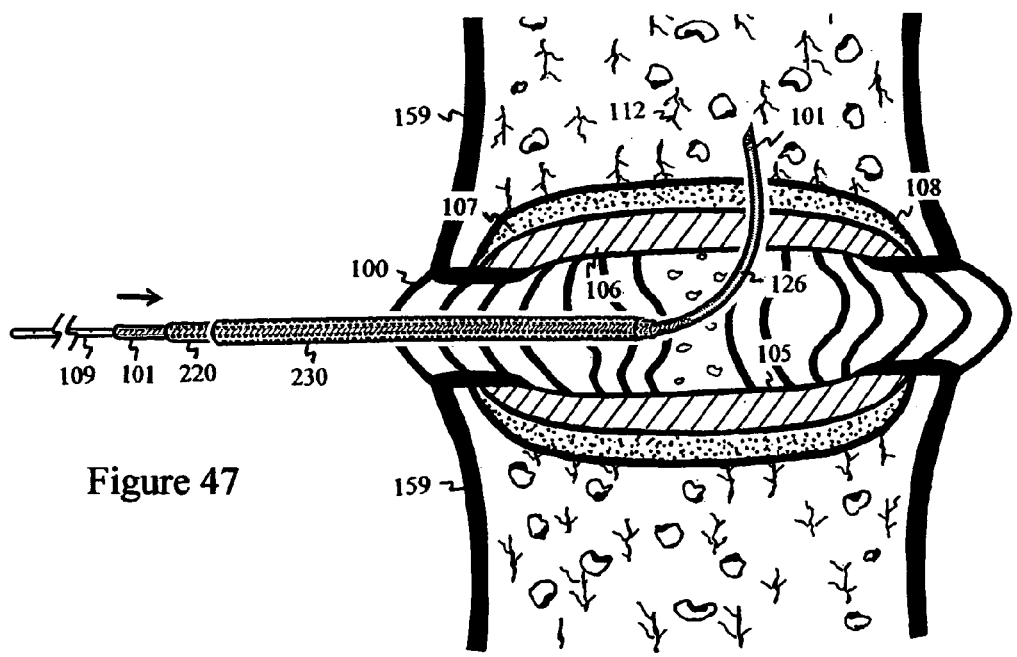
FIG. 47 shows deployment of the curved needle 101 through the calcified endplate 105.
Figure 48:
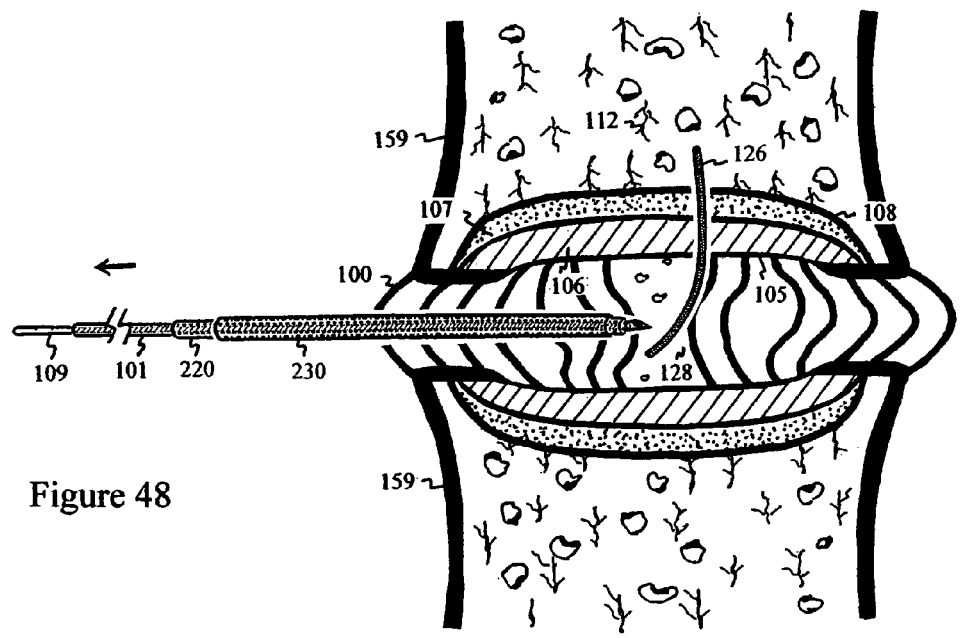
FIG. 48 depicts withdrawal of the needle 101 while the plunger 109 is held stationary to dislodge the conduit 126 through the calcified endplate 105.
Figure 49:
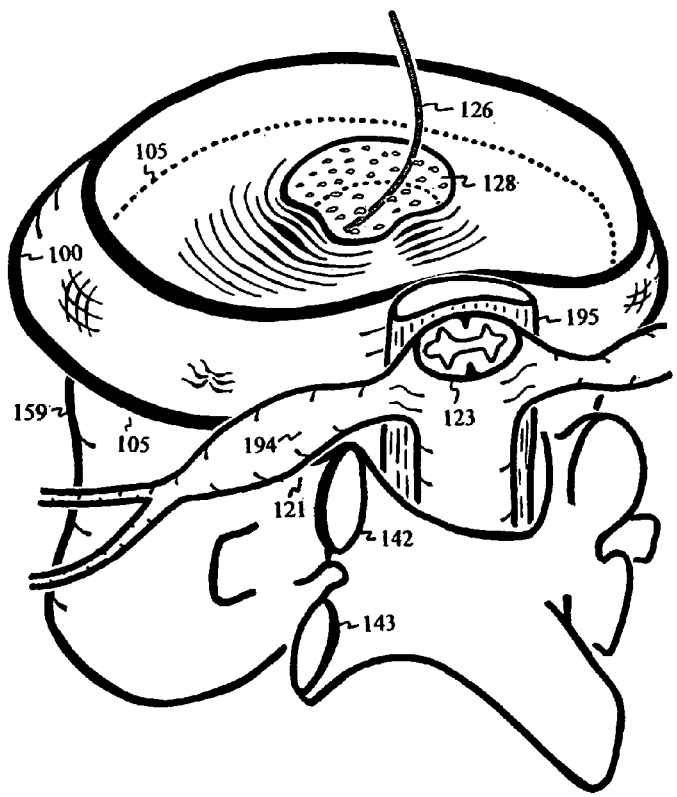
FIG. 49 shows a portion of the conduit 126 within the nucleus pulposus 128 and the remaining portion within the vertebral body through the endplate (not shown).

FIG. 46 depicts insertion of the needle 101, conduit 126, plunger 109, sleeve 220 and dilator 230 into the disc 100. The resiliently straightened needle 101 carrying the conduit 126 is deployed from the sleeve 220, resumes the curvature and punctures through the endplate 105 and calcified layers 108, as shown in FIG. 47. While the plunger 109 behind the conduit 126 is held stationary, the elastically curved needle 101 is withdrawn from the calcified endplate 105 and retrieved into the sleeve 220 to deploy, expel or dislodge the conduit 126 at the calcified endplate 105, as shown in FIG. 48. The conduit 126 acts as a channel or a passage, bridging between the bone marrow of the vertebral body 159 and the disc 100 to re-establish the exchange of fluid, nutrients, gases and wastes. FIG. 49 shows the general location of the conduit 126 between the disc 100 and the vertebral body through the calcified endplate (both not shown).

Figure 50:
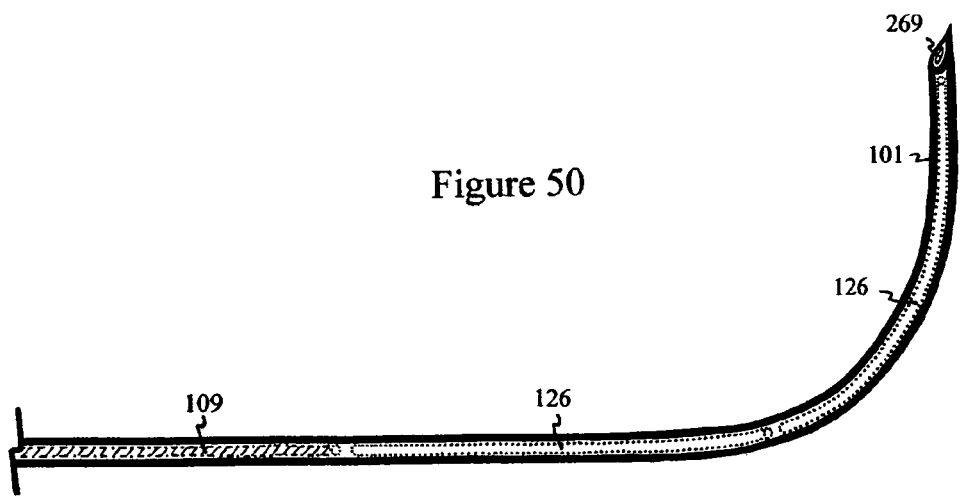
FIG. 50 depicts two conduits 126 within the lumen 269 of the needle 101.
Figure 51:
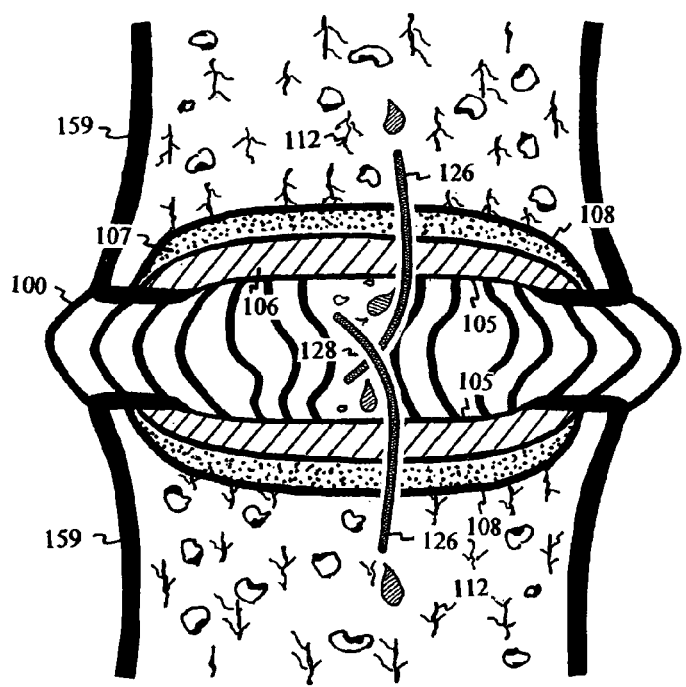
FIG. 51 shows deployment of two conduits 126 through superior and inferior calcified endplates 105.

Multiple conduits 126 can be loaded in series into the curved needle 101, as shown in FIG. 50. Each conduit 126 is deployed sequentially at the calcified endplate 105 by retrieving the curved needle 101 and holding the plunger 109 stationary. In essence, the plunger 109 is advanced toward the distal end of the needle 101 one conduit-length at a time. After deploying the first conduit 126 at the cranial endplate 105, the rigid sleeve 220 is rotated 180° to deploy the second conduit 126 into the caudal endplate 105, as shown in FIG. 51. Multiple conduits 126 within the elastically curved needle 101 allow surgeons to implant multiple conduits through calcified endplates 105 without having to withdraw the needle 101 assembly, reload additional conduits 126 and re-insert the assembly into the disc 100.

In the supine position, disc pressure is low. During sleep, fluid is drawn in by the water absorbing glycosaminoglycans within the nucleus pulposus 128. By bridging the calcified endplate 105, the glycosaminoglycans draw fluid with sulfate, oxygen and other nutrients through the conduits 126 into the nucleus pulposus 128 during sleep by (1) capillary action, and (2) imbibing pull of the water-absorbing glycosaminoglycans. The flow of sulfate, oxygen and nutrients is channeled within the conduit 126 unidirectionally toward the nucleus pulposus 128, rather than via the dispersion mechanism in diffusion.

Figure 52:
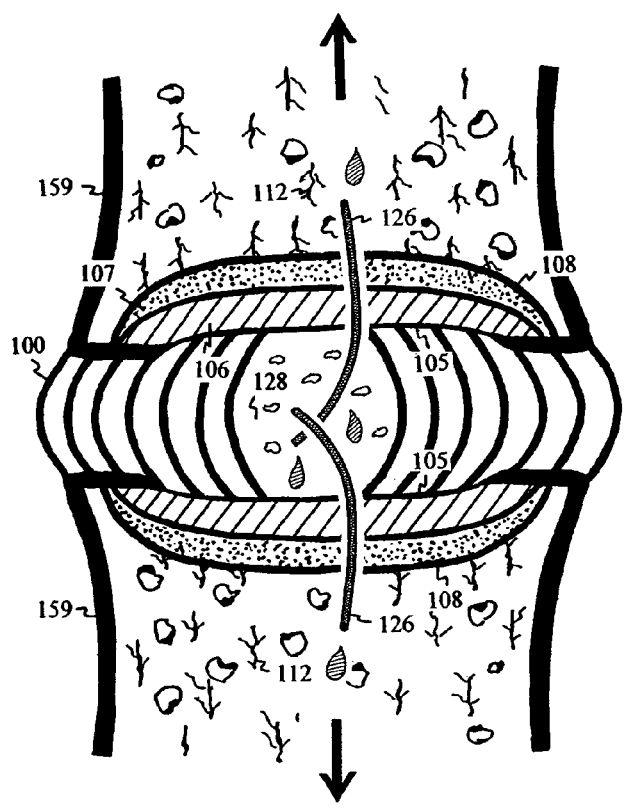
FIG. 52 indicates disc 100 height restoration from regained swelling pressure within the nucleus pulposus 128 following the re-establishment of nutrient and waste exchange.
Figure 53:
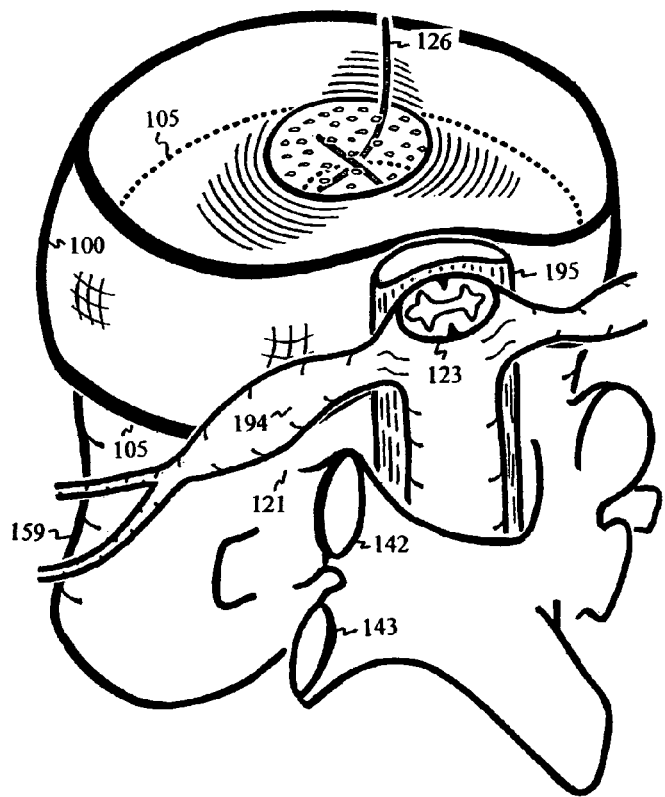
FIG. 53 depicts two conduits 126 extending from the nucleus pulposus 128 into superior and inferior vertebral bodies 159 through the calcified endplates 105 (not shown).

It is generally accepted that disc 100 degeneration is largely related to nutritional and oxygen deficiency. By re-establishing the exchange, a renewed and sustained supply of sulfate may significantly increase the production of sulfated glycosaminoglycans and restore swelling pressure. Restoration of swelling pressure within the nucleus pulposus 128 reinstates the tensile stresses within the collagen fibers of the annulus, thus reducing the inner bulging and shear stresses between the layers of annulus, as shown in FIG. 52. Similar to a re-inflated tire, disc 100 bulging is reduced and nerve impingement is minimized. Thus, the load on the facet joints 129 is also reduced to ease pain, the motion segment is stabilized, and disc 100 space narrowing may cease. The progression of spinal stenosis is halted and/or reversed, as shown in FIG. 53 to ease pain.

In daily activities, such as walking and lifting, pressure within the disc 100 greatly increases. Direction of the convective flow then reverses within the conduit 126, flowing from high pressure within the disc 100 to low pressure within vertebral bodies 159. The lactic acid and carbon dioxide dissolved in the fluid within the nucleus pulposus 128 is slowly expelled through the conduit 126 into the vertebral bodies 159, then to bodily circulation. As a result, the lactic acid concentration decreases, and pH within the disc 100 is normalized.

Furthermore, due to the abundance of oxygen in the disc 100 supplied through the conduit 126, lactic acid normally produced under anaerobic conditions may drastically decrease. Hence, the pain caused by acidic irritation at tissues, such as the posterior longitudinal ligament 195, superior 142 and inferior 143 articular processes of the facet joint, shown in FIG. 53, is anticipated to quickly dissipate. Buffering agents, such as bicarbonate, carbonate or others, can be loaded or coated on the conduits 126 to neutralize the lactic acid upon contact and spontaneously ease the pain.

The elasticity of the curved needle 101 still can twist within the rigid sleeve 220 during endplate 105 puncturing, as shown in FIG. 54. The likelihood of twisting increases with the length of the elastic needle 101. The twisting is depicted in a cross-sectional view of the sleeve 220, needle 101 and conduit 126 in FIG. 55. The elastic twisting between the shafts of the needle 101 and sleeve 220 allows directional shift at the tip of the needle 101 during contact with the calcified endplate 105. As a result, puncturing of the endplate 105 may fail.

To avoid twisting, the cross-sections of the needle 101 and sleeve 220 can be made non-round, such as oval in FIG. 56 with a cross-sectional view in FIG. 57. A square cross-section is shown in FIG. 58. A rectangular cross-section is shown in FIG. 59. A triangular cross-section is in FIG. 60.

Figures 61, 62, 63:
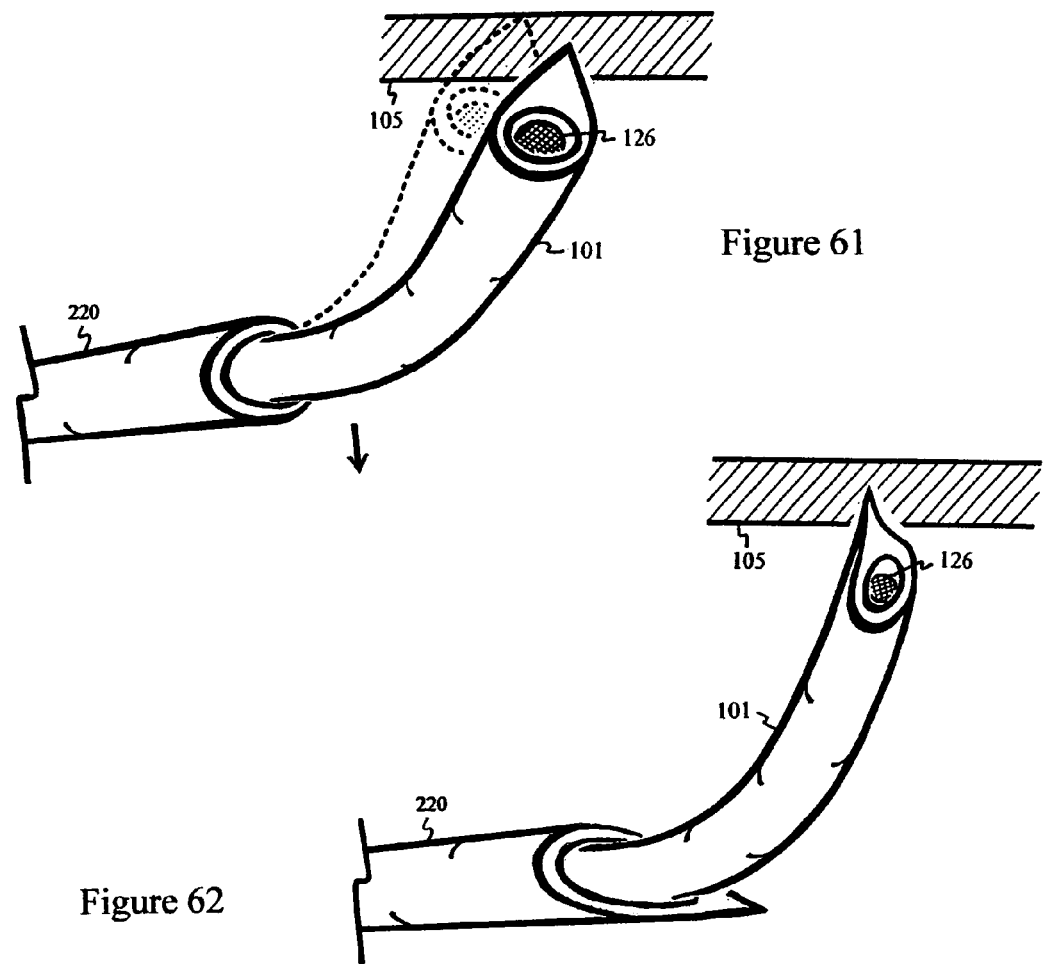
FIG. 61 depicts bending or drooping of the curved needle 101 during endplate 105 puncturing.
FIG. 62 shows a sharpened end or tip of the rigid needle 220 providing support beneath the convex side of the curved needle 101 to reduce bending or drooping during puncturing.
FIG. 63 depicts an extended distal end of the rigid needle 220 to lengthen the support beneath the convex side of the curved needle 101 during endplate 105 puncturing.

The elastic property of the curved needle 101 may bend and fail to penetrate through the calcified endplate 105, as shown in FIG. 61. The direction of the bend or droop is at the convex side of the curvature of the needle 101. To minimize the droop, the distal end of the rigid sleeve 220 is cut at an angle, providing an extension to support the convex side of the curved needle 101 during endplate 105 puncturing, as shown in FIG. 62. The angled cut of the rigid sleeve 220 functions as a rigid needle 220 with a sharp tip supporting the convex side of the curved needle 101, as shown in FIG. 62. The supporting structure can be further extended by cutting an indentation near the distal end of the rigid needle 220, as shown in FIG. 63, to increase support of the convex side of the curved needle 101 during endplate 105 puncturing.

Figure 64:
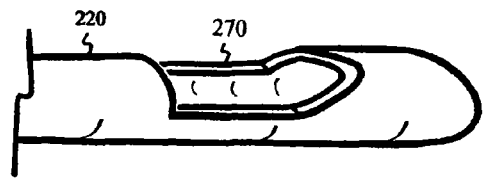
FIG. 64 shows a window 270 near the distal end of a sleeve 220 with an elliptical cross-section. The distal portion of the window 270 is slanted or sloped to conform to the curved needle 101.
Figure 65:
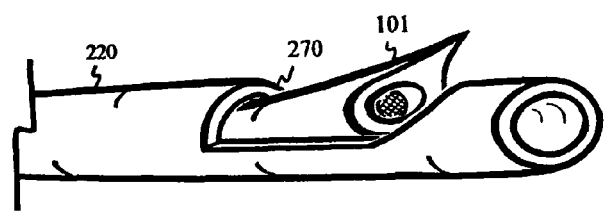
FIG. 65 depicts the sharp tip of the elastically curved needle 101 located on the concave side of the curvature for ease of protrusion through the window 270.
Figure 66:
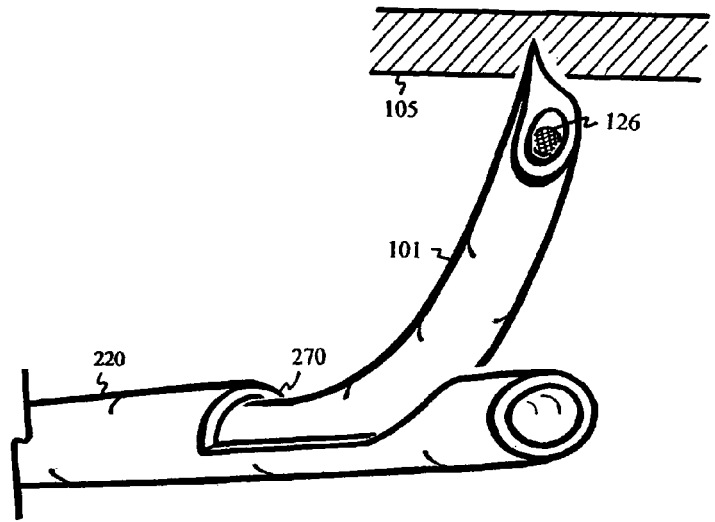
FIG. 66 shows support of the convex side of the curved needle 101 by the distal pocket of the window 270 to strengthen the needle 101 to puncture endplate 105.
Figure 67:
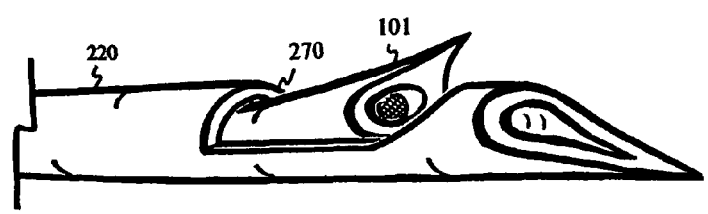
FIG. 67 shows a rigid needle 220 with the window 270.

To further support the elastically curved needle 101, a window 270 may be located near the distal end of the rigid sleeve 220 with an oval cross-section, as shown in FIG. 64. The distal side of the window 270 is open slanted at an angle. The slant can also be formed with multiple angles into a semi-circular-like pocket, sized and configured to fit the convex side of the elastically curved needle 101. FIG. 65 shows protrusion of the elastically curved needle 101 from the window 270 of the rigid sleeve 220. The sharp tip of the curved needle 101 is located on the concave side of the curvature to avoid scraping or snagging on the distal portion of the window 270 during deployment. FIG. 66 shows deployment of the elastically curved needle 101 from the window 270 of the rigid sleeve 220. The semi-circular pocket of the distal window 270 supports and brackets around the base of the convex curvature to minimize bending, twisting and/or deflection of the curved needle 101 during endplate 105 puncturing. In essence, the slanted portion of the window 270 provides a protruded pocket to direct and support the curved needle 101. The distal end of the rigid sleeve 220 can be sharpened to function as a rigid needle 220 with the window 270, as shown in FIG. 67.

When a substantial amount of bone is formed, puncturing through the bony endplate 105 with a small curved needle 101 can be challenging. Increasing the size of the needle 101 and creating a large hole 224 at the endplate 105 may cause leakage of nucleus pulposus 128 into the vertebral bodies 159. To support a small curved needle 101, a shape memory extension 271 containing a curvature similar to the curved needle 101 is added to strengthen and support the elastically curved needle 101, as shown in FIG. 68. The shape memory extension 271 can be indented, as shown in FIG. 68, or tubular at the distal end. The curved needle 101 and shape memory extension 271 are capable of sliding independently within the rigid sleeve or needle 220. FIG. 69 shows resiliently straightening of both the curved needle 101 and shape memory extension 271 within the rigid sleeve 220. Both the curved needle 101 and shape memory extension 271 apply stresses on the rigid sleeve 220. To minimize potential bending of the rigid sleeve 220, the stresses are distributed over a larger area by positioning the tip of the needle 101 proximal to the curvature of the shape memory extension 271, as shown in FIGS. 68-69. Spreading of the stresses also helps to ease the deployment and retrieval of both the needle 101 and shape memory extension 271.

For tissue puncturing, the shape-memory extension 271 is deployed from the rigid sleeve 220, as shown in FIG. 68, followed by the curved needle 101 gliding along the curvature of the shape-memory extension 271 and puncturing into the calcified endplate 105, as shown in FIG. 70. The shape memory extension 271 provides support to the needle 101 to minimize bending and twisting during puncturing without increasing the size of the puncture. The shape memory extension 271 can also be non-indented and sharpened to facilitate tissue piercing, as shown in FIG. 71. To dislodge the conduit 126 at the endplate 105, the plunger 109 behind the conduit 126 is held stationary, while the curved needle 101 is retrieved into the shape memory extension 271. The shape memory extension 271 is then withdrawn into the rigid sleeve 220.

Figure 72:
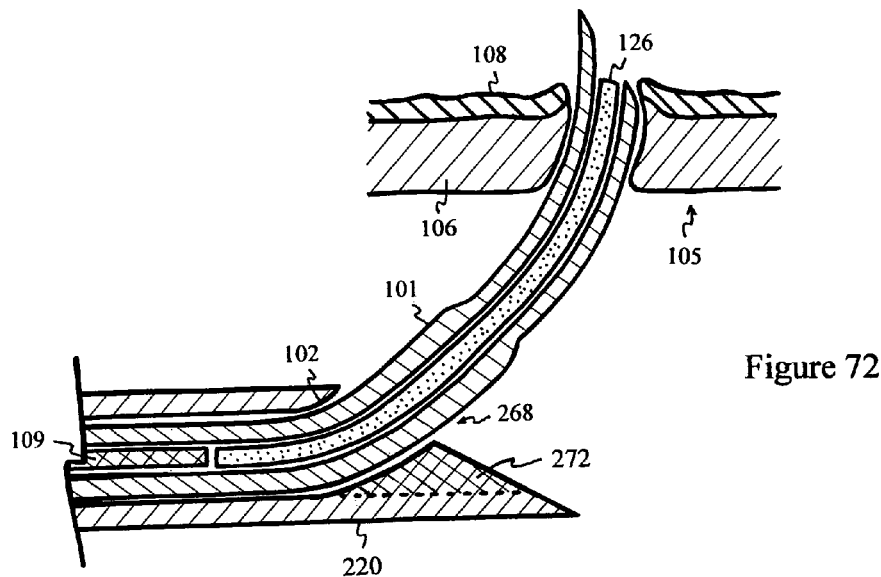
FIG. 72 shows a longitudinal cross section of a curved needle 101 with non-uniform outer diameter, supported by a ramp 272 within the lumen 268 of the rigid needle 220.

The outer diameter of the curved needle 101 can be made non-uniform, being small at the distal end for creating a small opening, as shown in FIG. 72. The adjoining curved portion of the needle 101 contains a thick wall and a larger outer diameter to support and strengthen the process of endplate 105 puncturing. The transition between the small and large outer diameters is gradual, as shown in FIG. 72, or in steps. The curved needle 101 with varying outer diameters can be made by grinding, machining or injection molding.

The lumen 268 of the rigid needle 220 may have a bevel 102 and a double-sided ramp 272, as shown in FIG. 72. The bevel 102 or tapering at the distal end of the lumen 268 minimizes friction against the concave side of the curved needle 101 during deployment and retrieval. The double-sided ramp 272 is protruded at the side opposite to the bevel 102 with the distal side in continuation with the sharp tip or extended end of the rigid needle 101. The proximal side of the ramp 272 or protrusion can be shaped to conform to and support the convex side of the curved needle 101 during endplate 105 puncturing. The ramp 272 can be made with epoxy, solder or other hardened material, then shaped by machining. The ramp 272 can also be created during a molten process to seal the lumen 268 at the distal end. The sealed end is then cut, the ramp 272 and bevel 102 are shaped, and the lumen 268 is re-opened by machining.

Figure 73:
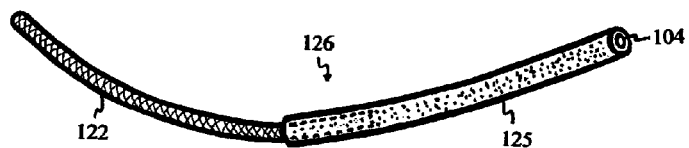
FIG. 73 depicts a conduit 126 containing a multi-filament 122 section and a tubular 125 section.

Sections of the conduit 126 are made to optimize the exchange of nutrients and waste. FIG. 73 shows a conduit 126 with braided filaments 122 connected to a porous tube 125 with a lumen 104. The tubular 125 portion acts as a funnel, collecting nutrients from capillaries within the vertebral body 159 and funneling the nutrients into braided filaments 122 within the nucleus pulposus 128.

Figure 74:
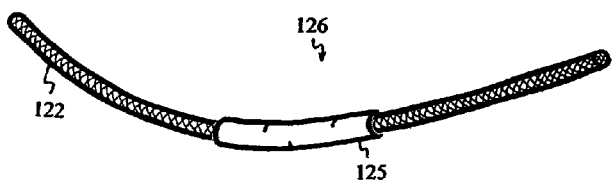
FIG. 74 shows a multi-filament 122 with a tube 125 at the mid-portion to prevent mineralization or clotting, especially around the endplate 105.

Especially at the endplate 105, mineralization within the pores or channels of the conduit 126 may occlude or block the exchange of nutrients and waste between the vertebral body 159 and disc 100. FIG. 74 shows a tube 125 covering or wrapped around the mid-section of the conduit 126 to prevent ingrowth of minerals or tissue into the pores or channels. The material for making the tube 125 can also have swelling, expanding or sealing characteristics to seal the puncture at the endplate 105 and prevent formation of Schmorl's node. The swelling, expanding or sealing material can be polyethylene glycol, polyurethane, silicon or others. An anti-ingrowth film or coating at the mid-section of the conduit 126 may also discourage mineralization or occlusion within the channels or pores to ensure long lasting exchange of nutrients and waste.

Especially within the vertebral body 159 or outer annulus, formation of fibrous tissue over the conduit 126 may occur, hindering the exchange of nutrient and waste. A portion of the conduit 126 can be coated, grafted, covalently bonded or ionic bonded with a drug to minimize fibrous formation. The drug can be actinomycin-D, paclitaxel, sirolimus, cell-growth inhibitor or fibrous tissue inhibitor.

Figure 75:
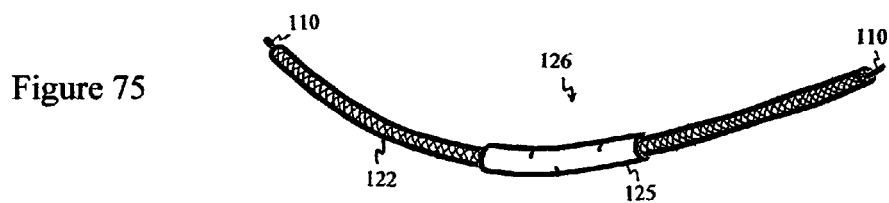
FIG. 75 depicts a monofilament 110 within the multi-filament 122 to assist deployment.
Figure 76:
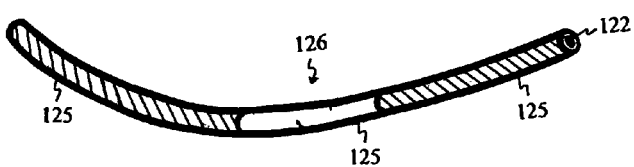
FIG. 76 shows degradable tubes (shaded) 125 covering both ends of a multi-filament 122 to prevent bunching during deployment from the curved needle 101.

Due to the soft or pliable characteristic, conduits 126 made with braided filaments 122 are difficult to deploy with the retrieving needle 101 and stationary plunger 109. A conduit 126 made with braided filament can be stiffened with water soluble agents, such as starch, collagen, hyaluronate, chondroitin, keratan or other biocompatible agents. After deployment, the soluble stiffening agent dissolves within the body, exposing the filaments to transport nutrients, oxygen and waste. FIG. 75 shows a monofilament 110 used as a stiff core within the braided conduit 126 to assist deployment. The monofilament 110 can be made with degradable material to maximize transport area after deployment of the conduit 126. Degradable tubes 125, indicated in the shaded area of FIG. 76, can also be used to wrap and stiffen the braided filaments 122. The degradable tube 125 or the degradable monofilament 110 can be made with poly-lactide, poly-glycolide, poly-lactide-co-glycolide or others.

Figure 77:
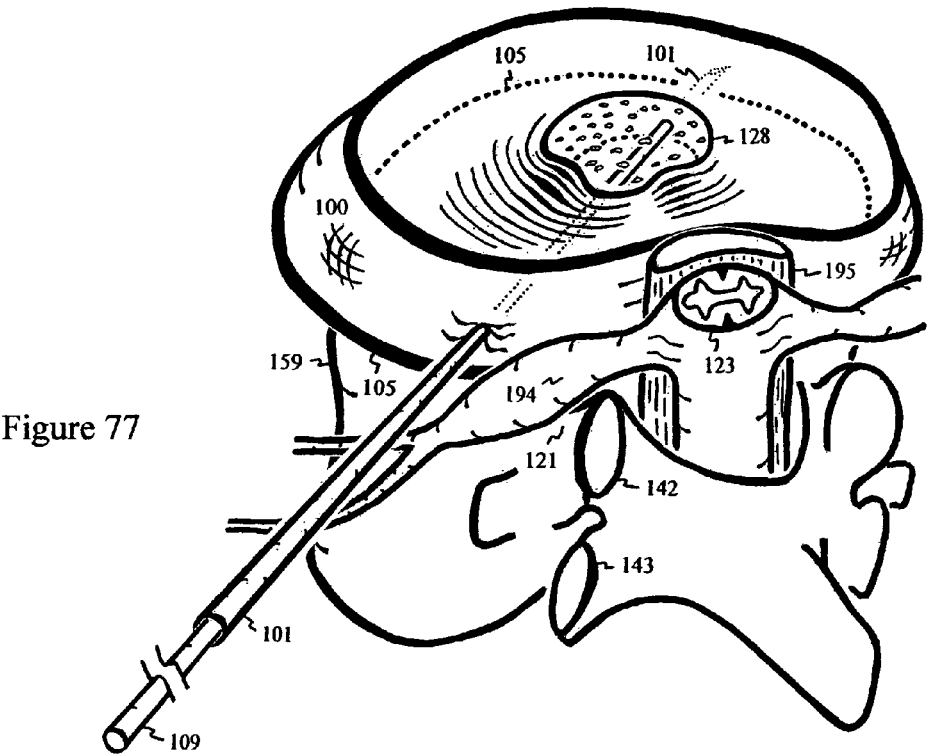
FIG. 77 shows the needle 101 carrying the conduit 126 transverse the degenerating disc 100.
Figure 78:
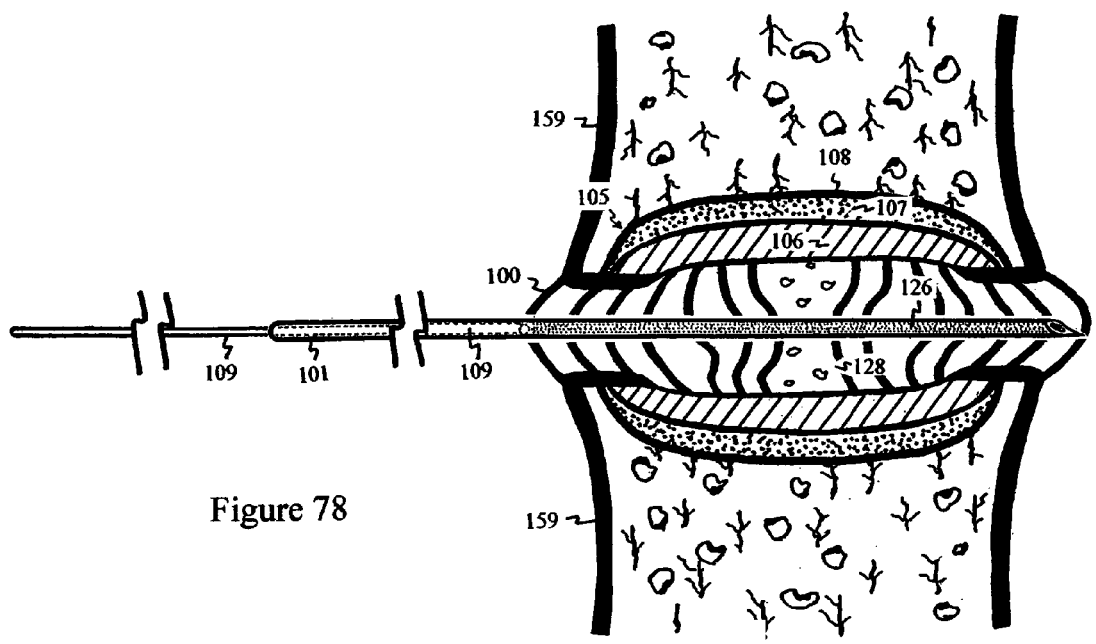
FIG. 78 depicts a longitudinal view of FIG. 84 to deliver a conduit 126 transverse a degenerating disc 100.

Since nutrients are relatively abundant within the peripheral 1 cm of the disc 100, the conduit 126 can also draw nutrients from the outer annulus through capillary action into the nucleus pulposus 128. A needle 101 carrying the starch-stiffened conduit 126 (not shown) and a plunger 109 is punctured into a disc 100 with calcified endplates 105, as shown in FIG. 77. The needle 101 guiding technique is similar to the one used in diagnostic injection of radiopaque dye for discography or chymopapain injection for nucleus pulposus 128 digestion to treat herniated discs 100. Guided by anteroposterior & lateral views from fluoroscopes, the needle 101 enters posteriolaterally, 45° from mid-line into the disc 100. A longitudinal view of the needle 101 carrying the stiffened conduit 126 puncturing through the disc 100 with calcified endplates 108 is shown in FIG. 78.

Figure 79:
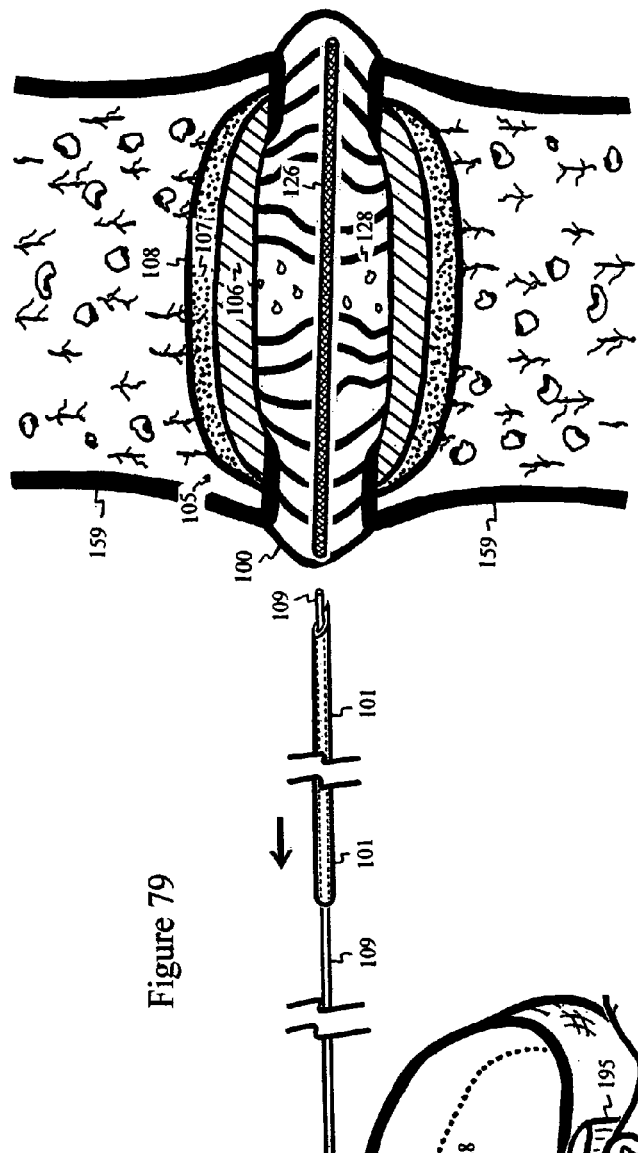
FIG. 79 depicts withdrawal of the needle 101 while holding the plunger 109 stationary to deploy or dislodge the conduit 126 within the degenerating disc 100.
Figure 80:
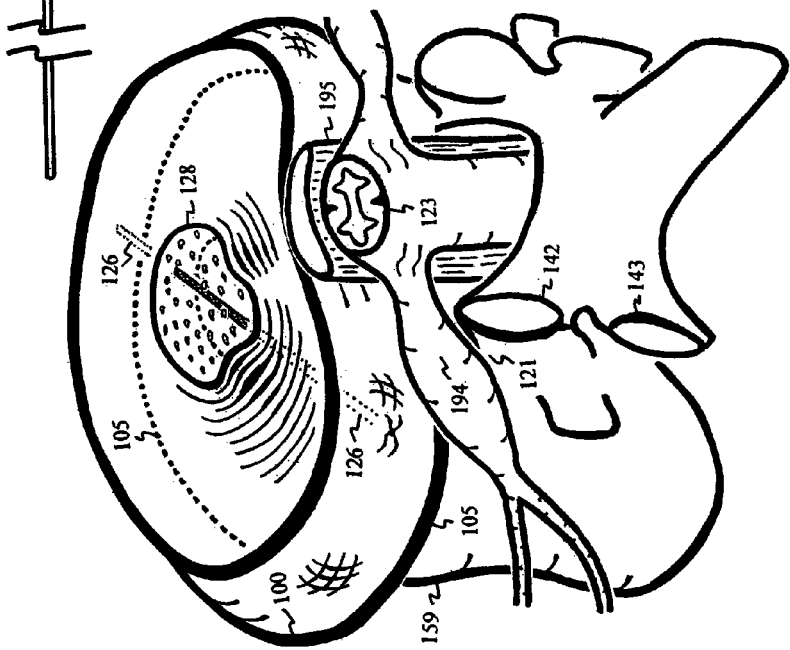
FIG. 80 depicts drawing of nutrients from the outer annulus into the nucleus pulposus 128 through capillary action or convection flow within the conduit 126.

By holding the plunger 109 stationary while the needle 101 is being withdrawn, the conduit 126 is dislodged from the lumen of the needle 101 and deployed across the disc 100, as shown in FIGS. 79-80. At least one end of the conduit 126 is placed less than 1 cm from the periphery of the disc 100 to draw nutrients and drain lactic acid. To enhance imaging, the section of the needle 101 containing the conduit 126 can be coated with a radiopaque, echogenic or magnetic coating 163, as shown in FIG. 81. Multiple conduits 126 can be safely and accurately deployed into different areas of a degenerating disc 100. FIG. 82 shows two conduits 126 deployed across a degenerating disc 100, exchanging nutrients and waste between the inner and outer disc 100.

In locations lacking any major blood vessel and organ, the tip of the needle 101 can be guided beyond the disc 100, as shown in FIG. 83, to deploy the conduit 126 beyond the disc

Figure 84:
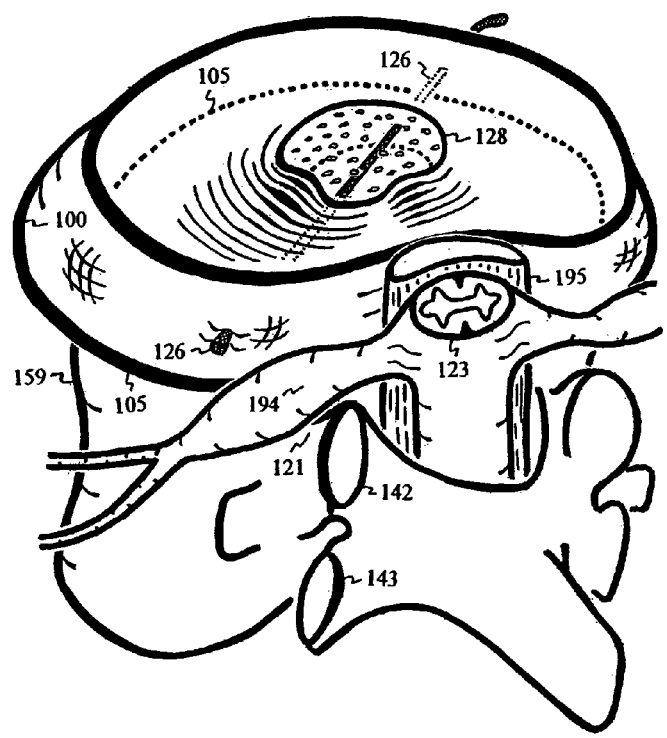
FIG. 84 shows the length of the conduit 126 extending beyond the disc 100 to maximize exchange of nutrients and waste.
Figure 85:
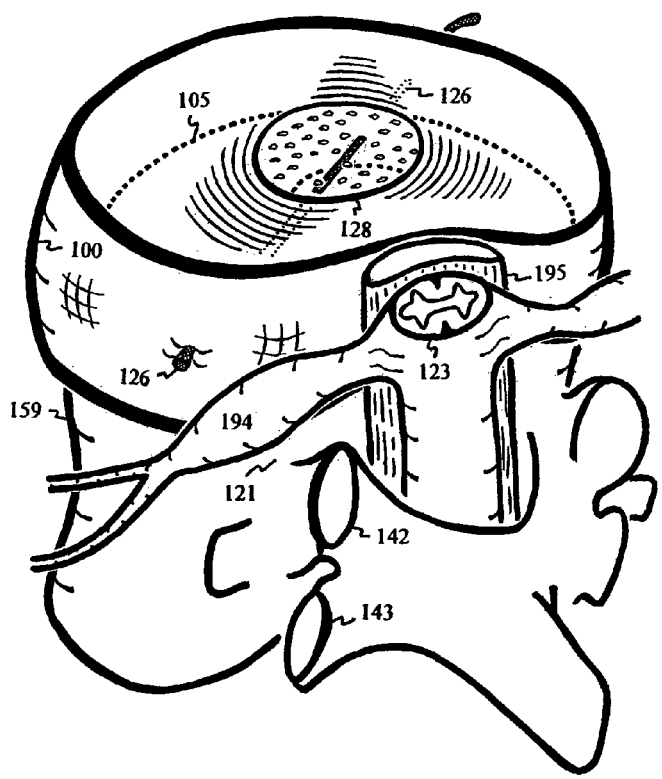
FIG. 85 depicts restoration of swelling pressure within the nucleus pulposus 128 enabling it to sustain compressive loading.

100, as shown in FIG. 84. The extended conduit 126 may draw significantly more nutrients into the disc 100. In addition, the extended conduit 126 may be more effective in disposing the waste generated within the disc 100 and expediting the repair and/or regeneration of the disc 100, as shown in FIG. 85.

Figure 86:
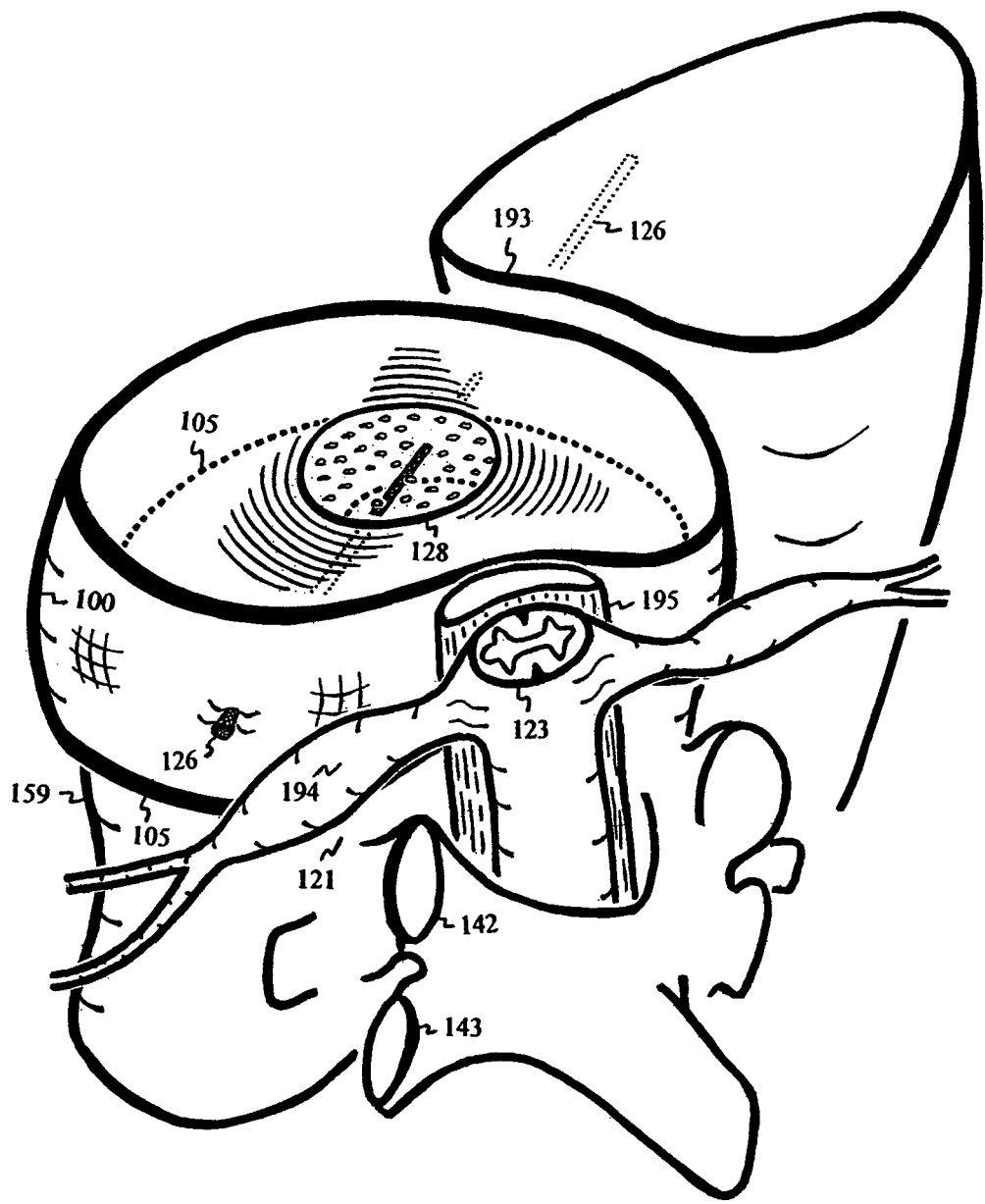
FIG. 86 shows a conduit 126 extending into the Psoas major muscle 193 for nutrient and waste exchange to nourish and/or regenerate the disc 100.
Figure 87:
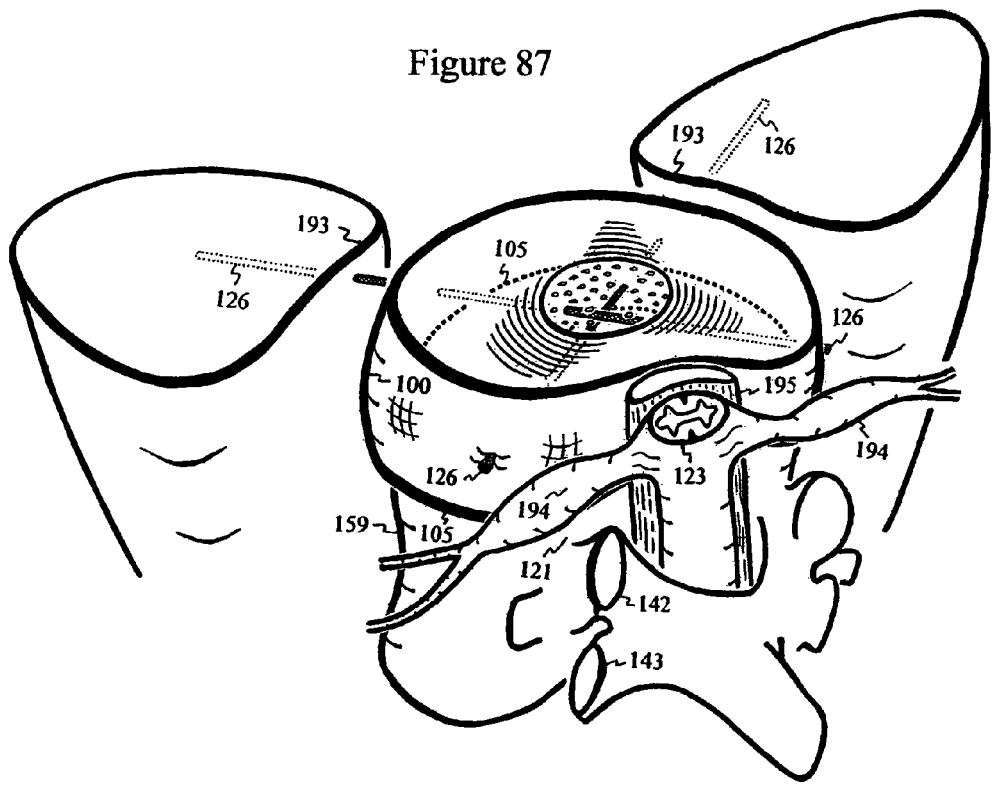
FIG. 87 depicts two conduits 126 extending into both Psoas major muscles 193 to expedite nutrient and waste exchange to nourish and/or regenerate the disc 100.

Psoas major muscles 193 are located adjacent to the lumbar segment of the spine. The needle 101 carrying the conduit 126 can puncture beyond the disc 100 into the muscle 193. As a result, the conduit 126 can draw nutrients from the muscle 193 into the disc 100, as shown in FIG. 86. Muscles 193 are well supplied with nutrients and oxygen, and muscles 193 dissipate lactic acid well. By extending into the muscles 193, the conduits 126 can draw an abundant amount of nutrients and safely deposit the waste from the inner disc 100 to repair or regenerate the degenerating disc 100, as shown in FIG. 87. The supple and tensionless conduits 126 are expected to be free from interfering with the functions of the disc 100 and muscles 193.

Methods and devices for conduit 126 deployments can also be in various combinations. The conduits 126 can be delivered into the endplates 105, as shown in FIG. 53, and transverse the annulus, as shown in FIG. 82 or 87.

An accelerated disc degeneration model was developed using rat tails. A tail section involving three discs was twisted or rotated 45° and held for 2 weeks. The section was then compressed by coil springs and held for an additional period of time. All discs within the section degenerated. Discs that had received additional nucleus pulposus from donor discs by injection experienced a delay in degeneration. Furthermore, insertions of the additional nucleus pulposus prior to the destructive loads provided the longest delay against disc degeneration.

After lumbar fusion procedures, the intervertebral discs 100 of adjacent free motion segments degenerate quickly. The degenerative process leads to more pain and possibly more surgery; following each new fusion is a new vulnerable segment adjacent to it. Accelerated degeneration of segments adjacent to a lumbar fusion may be the result of additional post-fusion stress and load. In the rat model, the added volume within the nucleus pulposus had a protective function against the destructive load. In conjunction with spinal fusion procedures, implanting conduits 126 within discs 100 adjacent to the fused segment may provide adequate swelling pressure contributed by an abundant supply of sulfate and oxygen to delay and hopefully prevent adjacent disc 100 degeneration.

Figure 88:
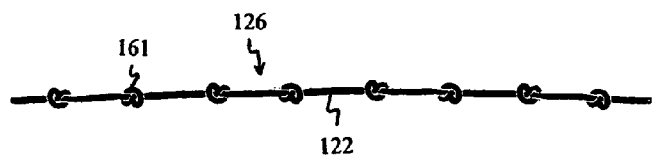
FIG. 88 depicts a series of knots 161 tied on a multi-filament 122 to prevent or minimize conduit 126 migration with time.
Figure 89:
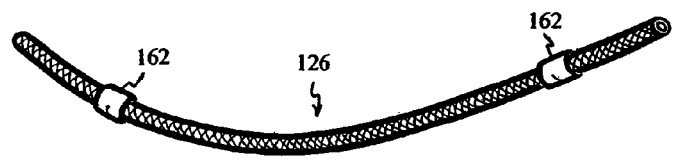
FIG. 89 shows rings 162 or protrusions on the conduit 126 to prevent or minimize migration with time.
Figure 90:
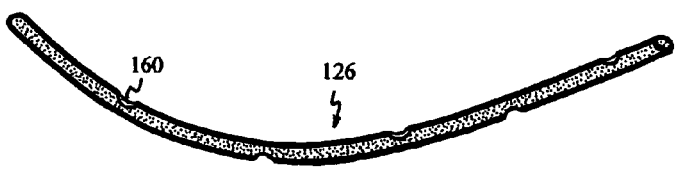
FIG. 90 shows indentations 160 to promote tissue ingrowth and prevent or minimize conduit 126 migration with time.

Device migration with time is always a concern. The average age of patients undergoing back surgery is 40-45 years old. The conduit 126 is expected to remain in place within the patients for fifty or more years. Migration of the tensionless conduits 126 may result in loss of effectiveness, but it is not likely to be detrimental to nerves, ligaments, muscles or organs. To minimize migration, knots 161 can be tied on the braided conduit 126, as shown in FIG. 88, to anchor within the annulus, endplate 105 and/or muscle 193. Similar to knots 161, rings 162 or protruded components 162 can be crimped on the conduit 126, as shown in FIG. 89. Both the knots 161 and the protrusions 162 are small enough to fit within the needle 101. Tissue ingrowth can also limit or prevent device migration. Indentations 160 or tissue ingrowth holes 160 can be created on the conduit 126, as shown in FIG. 90, to discourage migration with time.

The conduit 126 can also be used as a delivery vehicle to introduce healing elements for maintaining or regenerating the disc 100. The conduit 126 can be coated or seeded with growth factor, stem cells, donor cells, nutrients, buffering agent or minerals. Cells sensitive to sterilization can be loaded aseptically. Installations of conduits 126 can be in multiple stages, separated by days, weeks, months or even years. Initial conduit 126 deployment prepares the biological conditions, including pH, electrolytic balance and nutrients, to favor cell proliferation. Subsequent deployments may contain seeded cells within the conduit 126.

Since cellularity within the inner disc 100 is low, cell migration from the outer annulus or vertebral bodies 159 can be helpful in regenerating the degenerating disc 100. Cells can be transported along the convective flow within the conduit 126 into the nucleus pulposus 128. The channels or pores within the conduit 126 need to be sufficiently large, about 50 to 200 microns. For minerals, nutrients, lactic acid and gas exchange alone, the channels or pore size can be much smaller. Hence, the useful diameter of the capillary action channel or pore size of the conduit 126 has the range between 200 microns and 10 nanometers.

Potentially useful coating for the conduit 126 include antibiotic, anti-occlusive coating, lubricant, growth factor, nutrient, sulfate, mineral, buffering agent, sodium carbonate, sodium bicarbonate, alkaline, collagen, hydroxyapatite, analgesic, sealant, humectant, hyaluronate, proteoglycan, chondroitin sulfate, keratan sulfate, glycosamino-glycans, heparin, starch, stiffening agent, radiopaque coating, echogenic coating, cells or stem cells.

The tube 125 for preventing occlusion from mineralization or tissue ingrowth can be made with a biocompatible polymer, such as polytetrafluoroethylene, polypropylene, polyethylene, polyamide, polyester, polyurethane, silicon, poly-ether-ether-ketone, acetal resin, polysulfone, polycarbonate or polyethylene glycol. Similar material can be used to coat or partially coat the conduit 126 to prevent blockage of nutrient and waste transport. The coating should be able to withstand sterilization by gamma, electron beam, autoclave, ETO, plasma or UV light to prevent infection.

Especially for investigative purposes, a biodegradable conduit 126 may provide evidence within weeks or months. Since the conduit 126 degrades within months, any unforeseen adverse outcome would be dissipated. If the investigative-degradable conduit 126 shows promise, a permanent conduit 126 can then be installed to provide continuous benefits. The biodegradable conduit 126 can be made with polylactate, polyglycolic, poly-lactide-co-glycolide, polycaprolactone, trimethylene carbonate, silk, catgut, collagen, poly-p-dioxanone or combinations of these materials. Other degradable polymers, such as polydioxanone, polyanhydride, trimethylene carbonate, poly-beta-hydroxybutyrate, polyhydroxyvalerate, poly-gama-ethyl-glutamate, poly-DTH-iminocarbonate, poly-bisphenol-A-iminocarbonate, poly-ortho-ester, polycyanoacrylate or polyphosphazene can also be used. Similar biodegradable material can be used to make the biodegradable monofilament 110 in FIG. 75.

A wide range of non-degradable materials can be used to fabricate the conduit 126. Biocompatible polymers, such as polytetrafluoroethylene, polypropylene, polyethylene, polyamide, polyester, polyurethane, silicon, poly-ether-ether-ketone, acetal resin, polysulfone, polycarbonate, silk, cotton, or linen are possible candidates. Fiberglass can also be a part of the conduit 126 to provide capillarity for transporting nutrients and waste. Conduits 126 can also be made with metal, such as nickel-titanium alloy or stainless steel. Both non-degradable and degradable conduits 126 can be formed by molding, extruding, braiding, weaving, coiling, spiraling or machining. The conduits 126 can have a longitudinal lumen 104, pores and/or channels for fluid exchange. The conduit 126 can be a suture with a proven safety record. The conduit 126 can also be called or classified as a shunt, wick, tube, braided suture, braided filaments, thread or sponge. The disc 100 with the conduits 126 installed can be called the shunted disc 100.

The rigid needle 101, trocar 103, dilator 230 and plunger 109 can be made with stainless steel or other metal or alloy. The elastically curved needle 101, shape memory extension 271 and plunger 109 can be formed with nickel-titanium alloy. The needle 101, rigid needle 220, dilator 230, shape memory extension 271 and plunger 109 can be coated with lubricant, tissue sealant, analgesic, antibiotic, radiopaque, magnetic and/or echogenic agents.

Figure 91:
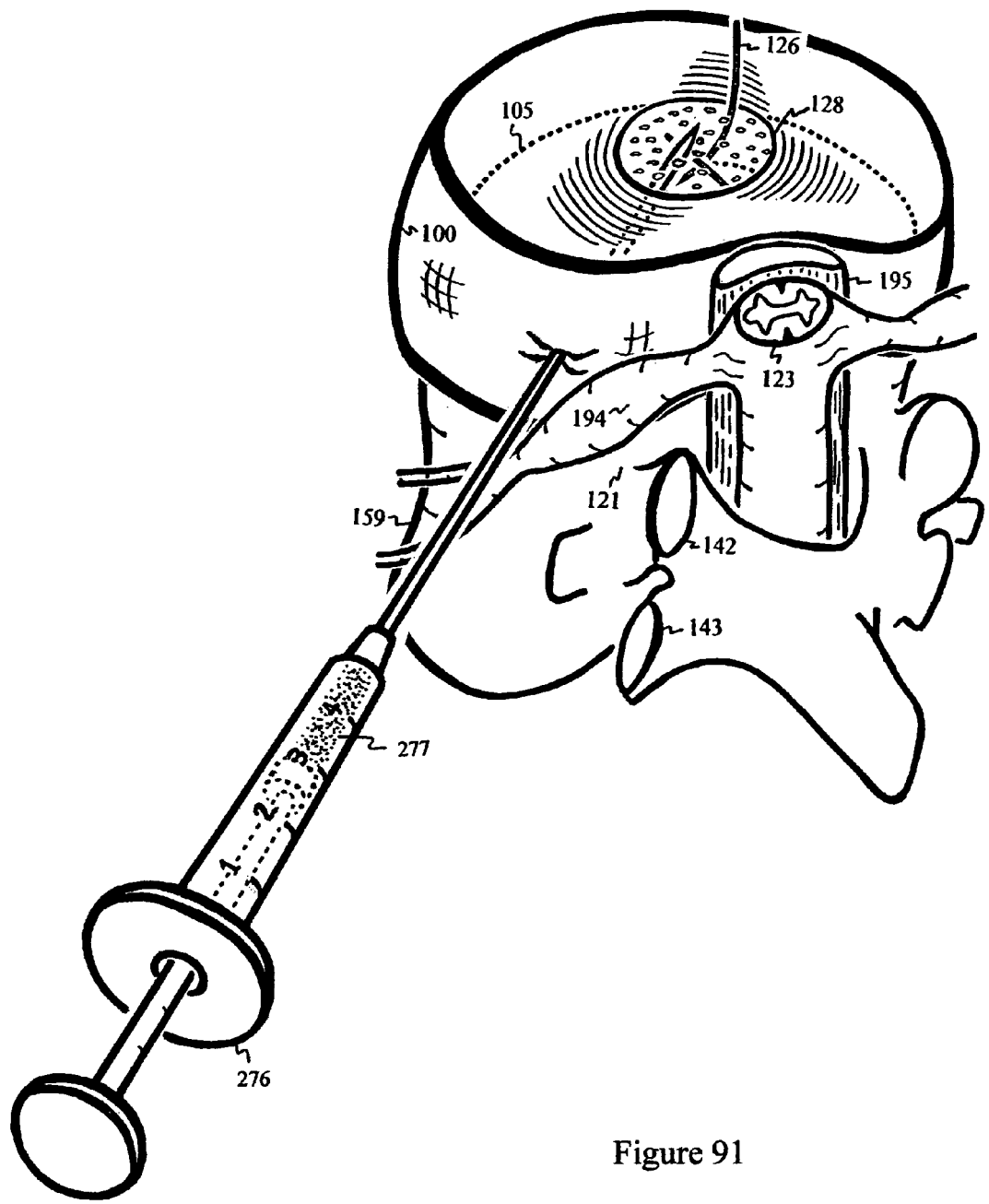
FIG. 91 shows injection of donor cells 277 through a syringe 276 into a disc 100 containing conduits 126 through cranial and caudal endplates 105.
Figure 92:
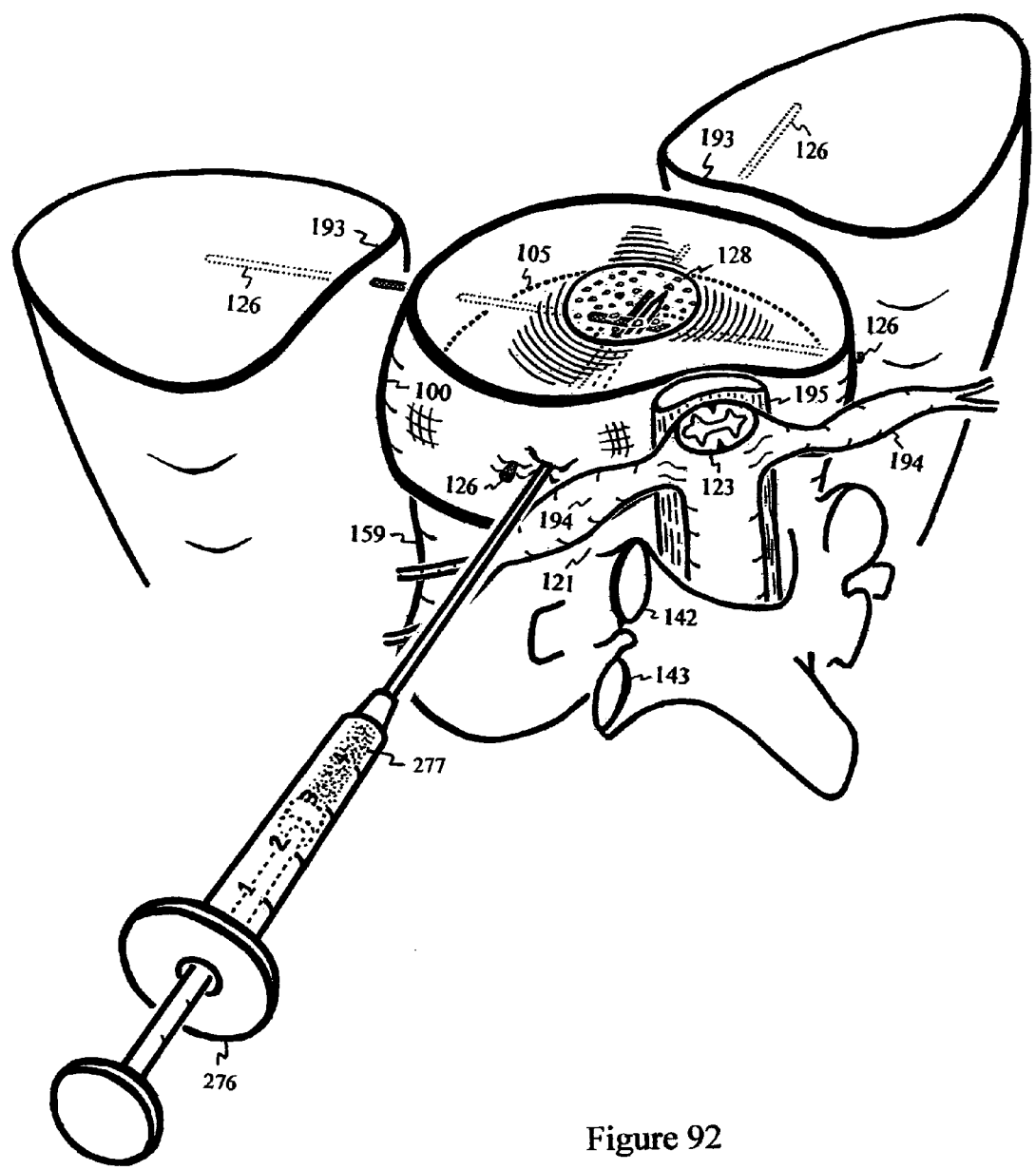
FIG. 92 shows injection of donor cells 277 through a syringe 276 into a disc 100 with conduits 126 transverse the disc 100 and extending into muscles 193.

Since nutrients and oxygen are extremely low particularly in degenerating discs 100, cell death is common, and healthy cells capable of producing glycosaminoglycans are few. Healthy cells 277 can be drawn from another disc 100 within the patient to inject with a syringe 276 into the degenerated disc 100, as shown in FIG. 91. Exchange of nutrients and waste is re-established through the newly installed conduits 126 through the cranial and caudal endplates 105 to nourish both the donor cells 277 and the remaining cells within the degenerating disc 100. Similarly, donor cells 277 can also be injected into the disc 100 with transverse conduits 126 to revitalize the disc 100, as shown in FIG. 92. Since cellularity within the degenerative disc 100 is low, introduction of donor cells 277 may expedite the process of halting or reversing disc degeneration.

The avascular disc 100 is well sealed. Even small ions, such as sulfate, and small molecules, such as proline, are greatly limited from diffusing into the nucleus pulposus 128. The well sealed disc 100 may be able to encapsulate donor cells 277 from a disc 100 of another person, cadaver or animal without triggering an immune response. For disc 100 regeneration, the donor cells 277 can also be stem cells 277, notochord 277 or chondrocytes 277. The semi-permeable conduits 126 are permeable to nutrients and waste but impermeable to cells, proteins, glycoproteins and/or cytokines responsible for triggering an immune reaction. The cells of the immune system include giant cells, macrophages, mononuclear phagocyts, T-cells, B-cells, lymphocytes, Null cells, K cells, NK cells and/or mask cells. The proteins and glycoproteins of the immune system include immunoglobulins, IgM, IgD, IgG, IgE, other antibodies, interleukins, cytokines, lymphokines, monokines and/or interferons.

The molecular weights of nutrients and waste are usually much smaller than the immuno-responsive cells, proteins and glycoproteins. The transport selectivity can be regulated or limited by the size of the pores or channels within the semi-permeable conduit 126. The upper molecular weight cut-off of the conduit 126 can be 3000 or lower to allow the passage of nutrients and waste but exclude the immuno-responsive cells, proteins, immunoglobulins and glycoproteins. The semi-permeable conduit 126 may also contain ionic or affinity surfaces to attract nutrients and waste. The surfaces of the semi-permeable conduit 126 can be selected or modified to repel, exclude or reject immuno-responsive components.

In recent years, cell transplants from cadavers or live donors have been successful in providing therapeutic benefits. For example, islet cells from a donor pancreas are injected into a type I diabetic patient's portal vein, leading into the liver. The islets begin to function as they normally do in the pancreas by producing insulin to regulate blood sugar. However, to keep the donor cells alive, the diabetic patient requires a lifetime supply of anti-rejection medication, such as cyclosporin A. In addition to the cost of anti-rejection medication, the long-term side effects of these immuno-suppressive drugs are uncertain. The benefit of cell transplant may not out weigh the potential side effects.

The intervertebral disc 100 with semi-permeable conduits 126 can be used as a semi-permeable capsule to encapsulate therapeutic donor cells 277 or agents, as shown in FIGS. 91 and 92, and evade the immune response; hence no life-long immuno-suppressive drug would be required. A variety of donor cells 277 or agent can be harvested and/or cultured from the pituitary gland (anterior, intermediate lobe or posterior), hypothalamus, adrenal gland, adrenal medulla, fat cells, thyroid, parathyroid, pancreas, testes, ovary, pineal gland, adrenal cortex, liver, renal cortex, kidney, thalamus, parathyroid gland, ovary, corpus luteum, placenta, small intestine, skin cells, stem cells, gene therapy, tissue engineering, cell culture, other gland or tissue. The donor cells 277 are immunoisolated within the discs 100, the largest avascular organs in the body, maintained by nutrients and waste transport through the semi-permeable conduits 126. The donor cells 277 can be from human, animal or cell culture. In the supine sleeping position, nutrients and oxygen are supplied through the conduits 126 to the donor cells 277. During waking hours while the pressure within the disc 100 is high, products biosynthesized by these cells 277 are expelled through the conduit 126 into the vertebral bodies 159, outer annulus or muscle 193, then into the veins, bodily circulation and target sites.

The product biosynthesized by the cells 277 within the shunted disc 100 can be adrenaline, adrenocorticotropic hormone, aldosterone, androgens, angiotensinogen (angiotensin I and II), antidiuretic hormone, atrial-natriuretic peptide, calcitonin, calciferol, cholecalciferol, calcitriol, cholecystokinin, corticotropin-releasing hormone, cortisol, dehydroepiandrosterone, dopamine, endorphin, enkephalin, ergocalciferol, erythropoietin, follicle stimulating hormone, γ-aminobutyrate, gastrin, ghrelin, glucagon, glucocorticoids, gonadotropin-releasing hormone, growth hormone-releasing hormone, human chorionic gonadotrophin, human growth hormone, insulin, insulin-like growth factor, leptin, lipotropin, luteinizing hormone, melanocyte-stimulating hormone, melatonin, mineralocorticoids, neuropeptide Y, neurotransmitter, noradrenaline, oestrogens, oxytocin, parathyroid hormone, peptide, pregnenolone, progesterone, prolactin, pro-opiomelanocortin, PYY-336, renin, secretin, somatostatin, testosterone, thrombopoietin, thyroid-stimulating hormone, thyrotropin-releasing hormone, thyroxine, triiodothyronine, trophic hormone, serotonin, vasopressin, or other therapeutic products.

The products (hormones, peptides, neurotransmitter, enzymes, catalysis or substrates) generated within the shunted disc 100 may be able to regulate bodily functions including blood pressure, energy, neuro-activity, metabolism, activation and suppression of gland activities. Some hormones and enzymes govern, influence or control eating habits and utilization of fat or carbohydrates. These hormones or enzymes may provide weight loss or gain benefits. Producing neurotransmitters, such as dopamine, adrenaline, noradrenaline, serotonin or γ-aminobutyrate, from the donor cells 277 within the shunted disc 100 can treat depression, Parkinson's disease, learning disability, memory loss, attention deficit, behavior problems, metal or neuro-related disease.

Release of the products biosynthesized by the donor cells 277 within the shunted disc 100 is synchronized with body activity. During activities of daily living, the pressure within the shunted disc 100 is mostly high to expel the products biosynthesized by the donor cells 277 into circulation to meet the demands of the body. In the supine position, the flow within the shunts 126 is reversed, bringing nutrients and oxygen into the disc 100 to nourish the cells 277. Using islets of Langerhans from the donor's pancreas as an example, production of insulin is induced in the shunted disc 100 during sleeping hours when glucose enters into the disc 100. During waking hours when disc pressure is high, insulin is expelled through the conduits 126 into circulation to draw sugars into cell membranes for energy production. At night, the insulin released from the shunted disc 100 is minimal to prevent the hypoglycemia. In essence, products biosynthesized by the donor cells 277 are released concurrent with physical activity to meet the demands of the body.

Some biosynthesized products from the donor cells 277 are appropriately deposited through the vertebral body 159, as shown in FIG. 91, then into bodily circulation. Other products may be more effectively transported through the outer annulus, as in FIG. 82, and diffused through the abdomen into bodily circulation. Some other products may be far more effective by entering into the muscles 193, as shown in FIG. 92.

Growth factors, buffering agents, hormones, gene therapeutic agents, nutrients, minerals, analgesics, antibiotics or other therapeutic agents can also be injected into the shunted discs 100, similar to FIGS. 91-92.

It is to be understood that the present invention is by no means limited to the particular constructions disclosed herein and/or shown in the drawings, but also includes any other modification, changes or equivalents within the scope of the claims. Many features have been listed with particular configurations, curvatures, options, and embodiments. Any one or more of the features described may be added to or combined with any of the other embodiments or other standard devices to create alternate combinations and embodiments. The conduit 126 can also have a gate to regulate rate and/or flow direction of nutrient, gas and waste exchange. It is also possible to connect a pump to the conduit 126 to assist the exchange between the disc 100 and the bodily fluid. A pH electrode may be exposed near the tip of the rigid needle 220 to detect the acidity within the disc 100.

It should be clear to one skilled in the art that the current embodiments, materials, constructions, methods, tissues or incision sites are not the only uses for which the invention may be used. Different materials, constructions, methods or designs for the conduit 126 can be substituted and used. Nothing in the preceding description should be taken to limit the scope of the present invention. The full scope of the invention is to be determined by the appended claims. For clarification in claims, sheath is a rigid tubular member. The elastically curved needle 101 can be called the elastic needle.

What is claimed is:

1. An elongated conduit for re-establishing exchange of nutrients and waste between an intervertebral disc and bodily circulation comprising:
   capillary action channels within said elongated conduit,
   a first portion, a middle portion and a second portion,
   and wherein said first portion is locatable within a patient's nucleus of the intervertebral disc, and said second portion is locatable within the patient's bodily circulation, thereby fluid is drawn through said capillary action channels to re-establish exchange of nutrients and waste between the intervertebral disc and bodily circulation.

2. The elongated conduit of claim 1, wherein said second portion is extended through an endplate and into a vertebra.

3. The elongated conduit of claim 1, wherein said second portion is extended outside the intervertebral disc.

4. The elongated conduit of claim 1, wherein said second portion is extended into a muscle.

5. The elongated conduit of claim 1, wherein said elongated conduit is a tube formed of a biocompatible material.

6. The elongated conduit of claim 1, wherein said elongated conduit is a multi-filament formed of a biocompatible material.

7. The elongated conduit of claim 6, wherein said multi-filament is braided.

8. The elongated conduit of claim 1, wherein said elongated conduit is a sponge formed of a biocompatible material.

9. The elongated conduit of claim 1, wherein said elongated conduit further comprises a plurality of protrusions extending therefrom.

10. The elongated conduit of claim 1, wherein said elongated conduit is formed of a multi-filament portion and a mono-filament portion.

11. The elongated conduit of claim 1, wherein said elongated conduit is formed of a biodegradable material.

12. The elongated conduit of claim 1, wherein said elongated conduit is formed of a non-degradable material.

13. The elongated conduit of claim 1, wherein said elongated conduit further comprises at least one indentation.

14. The elongated conduit of claim 1, wherein said capillary action channels having diameters ranging between 200 microns and 10 nanometers.

15. The elongated conduit of claim 1, further comprising a tube located around said middle portion of said conduit.

16. The elongated conduit of claim 15, wherein said tube is formed of a material chosen from the group of materials consisting of polytetrafluoroethylene, polypropylene, polyethylene, polyamide, polyester, polyurethane, silicon, polyether-ether-ketone, acetal resin, polysulfone, polycarbonate and polyethylene glycol.

17. The elongated conduit of claim 1, wherein at least a portion of said elongated conduit is coated with fibrous tissue inhibitor.

18. A treatment kit used to provide immunoisolated retention of donor cells within a patient's intervertebral disc: the elongated conduit of claim 1, and donor cells injectable into the intervertebral disc.

19. The treatment kit of claim 18, wherein the donor cells are from a gland.

20. The treatment kit of claim 18, wherein the donor cells are from tissue.

21. The treatment kit of claim 18, wherein the donor cells have an origin chosen from the group of origins consisting of the pituitary gland, hypothalamus, adrenal gland, adrenal medulla, fat cells, thyroid, parathyroid, pancreas, testes, ovary, pineal gland, adrenal cortex, liver, renal cortex, kidney, thalamus, parathyroid gland, ovary, corpus luteum, placenta, small intestine, skin cells, stem cells, gene therapy, tissue engineering and cell culture.

22. The treatment kit of claim 18, further comprising growth factor injectable into the intervertebral disc.

23. The treatment kit of claim 18, wherein the donor cells are capable of creating a therapeutic product.

24. The treatment kit of claim 18, wherein the donor cells are capable of creating a product chosen from the group of biosynthesized products consisting of adrenaline, adrenocorticotropic hormone, aldosterone, androgens, angiotensinogen (angiotensin I and II), antidiuretic hormone, atrial-natriuretic peptide, calcitonin, calciferol, cholecalciferol, calcitriol, cholecystokinin, corticotropin-releasing hormone, cortisol, dehydroepiandrosterone, dopamine, endorphin, enkephalin, ergocalciferol, erythropoietin, follicle stimulating hormone, gamma aminobutyrate, gastrin, ghrelin, glucagon, glucocorticoids, gonadotropin-releasing hormone, growth hormone-releasing hormone, human chorionic gonadotrophin, human growth hormone, insulin, insulin-like growth factor, leptin, lipotropin, luteinizing hormone, melanocyte-stimulating hormone, melatonin, mineralocorticoids, neuropeptide Y, neurotransmitter, noradrenaline, oestrogens, oxytocin, parathyroid hormone, peptide, pregnenolone, progesterone, prolactin, pro-opiomelanocortin, PYY-336, renin, secretin, somatostatin, testosterone, thrombopoietin, thyroid-stimulating hormone, thyrotropin-releasing hormone, thyroxine, triiodothyronine, trophic hormone, serotonin, and vasopressin.

* * * * *